United States Patent
Splett et al.

(10) Patent No.: US 6,599,242 B1
(45) Date of Patent: Jul. 29, 2003

(54) METHOD AND APPARATUS FOR DATA COMPRESSION OF HEART SIGNALS

(75) Inventors: Vincent E. Splett, Apple Valley, MN (US); Brian B. Lee, Golden Valley, MN (US); William J. Combs, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 44 days.

(21) Appl. No.: 09/619,296

(22) Filed: Jul. 19, 2000

(51) Int. Cl.$^7$ ............................................. A61B 5/00
(52) U.S. Cl. ..................... 600/300; 600/508; 345/440.1
(58) Field of Search ............................. 600/523, 524, 600/508, 300; 607/59, 9; 345/440, 440.1, 423, 442

(56) References Cited

U.S. PATENT DOCUMENTS

| | | | |
|---|---|---|---|
| 4,556,063 A | 12/1985 | Thompson et al. | 128/419 PT |
| 4,791,931 A | 12/1988 | Slate | 128/419 PG |
| 4,947,858 A | * 8/1990 | Smith | 600/509 |
| 5,217,021 A | * 6/1993 | Steinhaus | 600/509 |
| 5,312,446 A | 5/1994 | Holschbach et al. | 607/9 |
| 5,368,040 A | 11/1994 | Carney | 128/700 |
| 5,535,752 A | 7/1996 | Halperin et al. | 128/670 |
| 5,564,434 A | 10/1996 | Halperin et al. | 128/748 |
| 5,836,889 A | 11/1998 | Wyborny et al. | 600/509 |

OTHER PUBLICATIONS

"Arrhythmia detection porgram for an ambulatory ECG monitor," Biomed. Sci. 14:81–85, 1978.*

(List continued on next page.)

Primary Examiner—George R. Evanisko
Assistant Examiner—Roderick Bradford
(74) Attorney, Agent, or Firm—Girma Wolde-Michael; Michael C. Soldner

(57) ABSTRACT

An improved turning point system and method for performing data compression is disclosed. The system improves the conventional turning point compression method by selecting a predetermined number of the "best" turning points in the sample window including data samples $X_0$ and $X_N$. From this sample-window, ones of the data samples $X_1$ through $X_{(N-1)}$ will be identified as turning points using a selected one of a disclosed set of turning point detection methods. In one embodiment, a turning point is identified by determining that the slopes in the lines interconnecting adjacent data points have different polarities. In an alternative embodiment, a data sample $X_M$ is considered a turning point if the slope of the line between the data samples $X_M$ and $X_{(M+1)}$ has a different polarity as compared to the slope of the last waveform segment that was encountered that did not have a slope of zero. According to one mechanism, amplitude thresholding is used to detect whether an identified turning point is likely the result of noise such that the turning point status of the data sample should be disregarded. After data samples are identified as turning points, ones of the identified turning points are identified as the "best" turning points to be selected for retention. The best turning points may be identified by determining which waveform segment included within a sample window has the largest change of amplitude. An alternative embodiment detects which of the turning points has the greatest signal amplitude compared to a reference value. Yet another embodiment selects as the best turning point that point having an amplitude that differs the most from the amplitude of the first data sample in the sample window. Still other embodiments retain the turning point having an amplitude which is more positive, or alternatively, more negative, than the other data samples. According to one aspect of the invention, the compression ratio varies based on the frequency of the input waveform. In another embodiment, position data is retained to indicate the relative position of retained data samples as compared to the position of other retained data samples. This position data may be calculated at a frequency that is less than the frequency of the sampled data.

36 Claims, 17 Drawing Sheets

OTHER PUBLICATIONS

Huffman, D.A., "A method for the construction of mininum-redundancy codes." Proc. IEEE, 40:1098–1101, 1952.

Ziv, J. and Lempel, A., A universal algorighm for sequential data compression, IEEE Trans. Inform. Theory, IT–23, pp. 337–343, 1977.

"AZTEC, a pre–processing program for real–time ECG rhythm analysis" by Cox, J.R. et al., IEEE Trans. Biomed. Eng., BME–15, pp. 128–129, 1968).

"Scan–along polygonal approximation for data compression of electrocardiograms", by Ishijima, M. et al. IEEE Trans. Biomed. Engl, BME–26, pp. 723–729, 1983.

Data Compression—Techniques and Applications, p. 256–259, T.J. Lynch, in "Arrhythmia detection program for an ambulatory ECG monitor" (Biomed. Sci. Instrum. 14:81–85, 1978.

"Arrhythmia detection program for an ambulatory ECG monitor," Biomed. Sci. Instrum. 14:81–85, 1978.

* cited by examiner

FIG. 4

METHOD AND APPARATUS FOR DATA COMPRESSION OF HEART SIGNALS

FIELD OF THE INVENTION

The present invention relates to data compression of sampled physiological signals such as electrocardiogram signals; and, more particularly, to methods and apparatus for performing the data compression employing improved turning point methods.

BACKGROUND OF THE INVENTION

ElectroCardioGram (ECG) monitoring systems such as Holter monitors are available to be worn externally by a patient to record electrical signals produced by the heart. Other ElectroGraM (EGM) monitors may be implanted within the body of a patient to record similar cardiac signals. Such monitoring systems are described in U.S. Pat. No. 5,312,446 and in U.S. Pat. No. 4,947,858, both of which are assigned to the assignee of the current invention, and are incorporated herein by reference.

Monitoring systems often have storage limitations. Cost, size, power consumption, and the sheer volume of data over time have limited external real-time Holter monitors to recording, at most, only twenty-four hour data segments. As an alternative, multiple shorter segments of data may be recorded when an irregular heartbeat is either automatically detected by the monitor, or is felt by the patient who then initiates the data storage.

Storage constraints are even more severe in implantable EGM monitoring systems, wherein conserving both power and space are prime considerations. Many different types of therapy delivery devices are associated with such monitoring systems including pacemakers, pacemaker/cardioverter/defibrillators, heart pumps, cardiomyostimulators, ischemia treatment devices, and drug delivery devices. Most of these cardiac systems include electrode pairs located adjacent to, or in, a heart chamber for sensing a "near-field" EGM signals. Other systems have electrode pairs wherein both electrodes are implanted in the body with one of the electrodes being positioned at a predetermined distance from the heart and from the other electrode to perform sensing of "far-field" EGM signals, which may also be called "subcutaneous ECG" signals. In either case, the near-field or far-field EGM signals are filtered and amplified for recording the sampled EGM, and for deriving event signals. Some of these Implantable Medical Devices (IMDs) are adapted to provide a therapy in response to the detection of these event signals. For example, the detection of a particular signal may initiate the delivery of a drug, a pacing signal, or another type of electrical stimulus to the patient.

Many IMDs store selected EGM signal segments and event data in internal RAM. This data may be transferred to an external programmer via a telemetry link. U.S. Pat. No. 5,312,446, referenced above, describes a system for storing such data on a First-In, First-Out (FIFO) basis. Another such system is provided by the Reveal™ implantable loop recorder available from the MEDTRONIC® corporation. This device records a forty-two-minute segment of far-field EGM. When a patient detects an irregular heart beat, the patient uses a magnet to activate the device recording function so that the cardiac signals may be stored and later diagnosed by a clinician. The stored EGM data is periodically transmitted from device memory to an external programmer via a telemetry session.

Other types of physiological signals may also be stored by recording systems. Such signals include blood pressure signals associated with the heart chamber or adjoining blood vessels during the cardiac cycle. Blood temperature, blood pH, and a variety of blood gas-level indications may also be recorded. Recording systems for monitoring these types of signals are disclosed in commonly assigned U.S. Pat. Nos. 5,368,040, 5,535,752 and 5,564,434, and in U.S. Pat. No. 4,791,931, all incorporated by reference herein. The MEDTRONIC® Chronicle® implantable hemodynamic recorder employs the leads and circuitry disclosed in the above-incorporated, commonly assigned, '752 and '434 patents to record the EGM and absolute blood pressure values for certain intervals. The recorded data is periodically transferred to an external programmer via an uplink telemetry transmission.

As stated earlier, generally physiological signals of the type recorded by IMDs and external monitors are sensed by electrode pairs. The signals are then filtered, amplified, digitized, and stored in memory at a selected sampling frequency. The sampling frequency is selected based on the frequency components of the EGM or the ECG signal. Generally, a high enough sampling frequency is selected so that an accurate signal may be reconstructed and displayed later. At a sampling frequency of about 256 Hz, enough information is retained to accurately reconstruct visual displays of the ECG and EGM data. However, at this sampling rate, approximately twenty-two megabytes of storage space is required to record signal data over a twenty-four-hour period assuming each sample is stored as an 8-bit byte. At this rate, the storage requirements for even short EGM segments become prohibitive in IMDs given the inherent space and power constraints. Moreover, it would take up to five hours to transfer a twenty-four hour data segment employing current telemetry transmission techniques.

Because of these constraints, attempts have been made to lower sampling rates, and/or to compress the sampled data. Reducing the sampling rate from 256 Hz to 128 Hz significantly conserves available memory. In signals consisting of frequency components not greater than about 60 Hz, this sampling rate is adequate. However, some cardiac waveforms contain energy above 60 Hz. In these cases, the reduction in sampling rate results in loss of data. This may result in the loss of the slope and shape of the original waveform, making it difficult or impossible for the medical care providers to use the information to make a correct diagnosis.

Data compression techniques provide an alternative to merely reducing the sampling frequency. These techniques can be characterized as either "lossy" or "loss-less". When data is compressed using a "loss-less" method, it is possible to reconstruct the original waveform without losing information. Such non-distorting compression modes are exemplified by the Huffinan coding method and the Lempel-Ziv method, as described respectively in the following articles: Huffinan, D. A., "A method for the construction of minimum-redundancy codes", *Proc. IEEE*, 40:1098–1101, 1952; and Ziv, J.; and Lempel, A., "A universal algorithm for sequential data compression, *IEEE Trans. Inform. Theory*, IT-23, pp. 337–343, 1977.

Loss-less compression modes are computationally expensive, resulting in a more complex circuit design, increased power consumption, and a longer data processing time. These techniques may also require a considerable amount of memory to perform. Moreover, the compression rate that is achieved depends on the frequency content of the EGM and ECG signals. This frequency content will vary depending on the physiological condition being monitored. As a result, the amount of memory needed to store the compressed data cannot be determined in advance.

As an alternative to the use of a loss-less compression process, a lossy technique may be employed. Lossy techniques require less processing power to implement. The resulting system is therefore both smaller and more energy efficient. However, when data is compressed using a lossy method, some information is lost when the compressed data is used to re-construct the original waveform. For example, according to one approach, all "baseline" sample values of a cardiac signal that occur between the PQRST waveform complexes are discarded. This can reduce memory requirements by about fifty percent for a normal sinus rhythm. In general, this is not acceptable, however, because many types of cardiac signals including Ventricular Tachycardia (VT), Ventricular Fibrillation (VF), Sinus Tachycardia (ST), and Atrial Fibrillation(AF) include virtually no baseline segments. These are the heart rhythms of greatest interest during the diagnosis of a cardiac abnormality.

More sophisticated, "lossy" compression methods have been used for ECG storage in external devices. Examples of such techniques include the Amplitude-Zone-Epoch-Time-Coding (AZTEC) pre-processing software program. AZTEC is described in "AZTEC, a pre-processing program for real-time ECG rhythm analysis" by Cox, J. R. et al. (*IEEE Trans. Biomed. Eng.*, BME-15, pp. 128–129.,1968.) The AZTEC algorithm has been used to store ECG data for automatic analysis functions such as QRS detection, but it has proven to be generally inadequate for a visual presentation of the data.

Another lossy technique is the SAPA, or "fan" method described in the above-incorporated '858 patent, and is further discussed in "Scan-along polygonal approximation for data compression of electrocardiograms", by Ishijima, M. et al. (*IEEE Trans. Biomed. Eng.*, BME-26, pp. 723–729, 1983). This method uses a straight line approximation of the waveform to store the ECG data, and does not generally permit substantial data compression. This is because the error threshold is uniform over the entire input waveform. Therefore, the allowable error in the P-wave and T-wave regions limit the overall compression.

Yet another technique is referred to as the Coordinate-Reduction-Time-Encoding-System (CORTES). This mechanism may be used to achieve up to 10:1 data compression, as is described in "Data Compression—Techniques and Applications", Pg. 256–259, T. J. Lynch. However, this technique is not considered adaptable for use in IMDs because of the processing power required to compress and store the data points in real time.

Other lossy data compression techniques are based upon domain transforms and include the Discrete Cosine Transform (DCT), the Walsh Transform, the Harr Wavelet Transform and the Daubechies Wavelet Transform. These techniques are relatively computationally intensive and are batch oriented. This means that these methods operate on a block of sequential data points at one time, and therefore are not easily implemented in integrated circuit hardware.

Another lossy compression mechanism is called the Mueller "turning point" algorithm, as described by W. C. Mueller in "Arrhythmia detection program for an ambulatory ECG monitor" (*Biomed. Sci. Instrum.* 14: 81–85, 1978). This algorithm achieves a fixed two-to-one compression ratio. The algorithm utilizes the last saved data point ($X_0$) to determine which of the next two data points $X_1$ or $X_2$ to retain where $X_2$ is the data point more recent in time. According to this algorithm, $X_1$ will be retained if that data point is a "turning" point, meaning that the slope of the line between points $X_0$ and $X_1$ is positive whereas the slope of the line between $X_1$ and $X_2$ is negative, or vice versa. In other words. $X_1$ is retained if it is a "peak" or a "valley" in the waveform. Otherwise, $X_2$ is retained.

The turning point algorithm is relatively simple to implement in either hardware, software, or a combination thereof. Moreover, even though the algorithm is lossy, the compressed data can, in many instances, be used to reconstruct a signal that retains the important peaks and valleys of a physiological signal. If greater than two-to-one compression is desired, the output of one turning point process may be cascaded with another compression iteration to achieve four-to-one compression.

Although the turning point mechanism provides many important advantages over other data compression schemes, in some instances, the turning point algorithm can discard important information. This occurs when both $X_1$ and $X_2$ are turning points, and $X_2$ is a more important turning point than $X_1$. For example, $X_1$ and $X_2$ may represent the Q and R waves of the QRS complex, respectively. The turning point algorithm will retain the smaller Q wave and discard the larger R wave. When the EGM or ECG trace is reconstructed from the compressed data, both the amplitude and the general shape of the resulting waveform is distorted. The effects are compounded when the turning point algorithm is cascaded to provide four-to-one data compression.

What is needed is an improved method and apparatus for data compression adaptable for use in an implantable medical device or external monitor having limited memory capacity. This method and apparatus should provide a sufficiently high compression factor, should not require large amounts of processing power to complete, and should provide reconstructed waveforms that are clinically acceptable.

SUMMARY OF THE INVENTION

It is therefore the primary object of the invention to provide an improved data compression system and method;

It is another object of the invention to provide an improved data compression system and method that provides two-to-one data compression;

It is still another object of the invention to provide an improved data compression system and method that can be cascaded to provide increased data compression ratios;

It is a yet another object of the invention to provide a turning point method that retains the optimal turning point in a frame containing N data points;

It is a further object of the invention to provide a system using an improved turning point process to compress EGM data within an implantable medical device;

It is a further object of the invention to provide a system using an improved turning point method to compress data derived from physiologic sensors in an implantable medical device;

It is still another object of the invention to provide improved data compression capabilities without increasing power consumption;

It is yet another object of the invention to provide improved data compression capabilities without substantially increasing processing requirements;

It is still another object of the invention to provide an improved turning point system and method that uses the "largest unshared leg" of an input waveform to select a data sample to retain from among a predetermined number of consecutive turning points;

It is another object of the invention to provide an improved turning point system and method that uses the "largest peak" of an input waveform to select a data sample to retain from among a predetermined number of consecutive turning points;

It is still another object of the invention to provide an improved turning point system and method that uses a "greatest difference from $X_0$" to select a data sample to retain from among a predetermined number of consecutive turning points;

It is another object of the invention to provide an improved turning point system and method that uses "a largest positive peak" of an input waveform to select a data sample to retain from among a predetermined number of consecutive turning points;

It is yet a further object of the invention to provide an improved turning point system and method that uses "a least positive peak" of an input waveform to select a data sample to retain from among a predetermined number of consecutive turning points;

It is another object of the invention to provide an improved turning point system and method having selectable criterion for selecting a first predetermined number of turning points to retain from among a second predetermined number of consecutive turning points;

It is yet another object of the invention to provide an improved turning point system and method having a variable compression ratio depending on the frequency of the sampled input waveform;

It is yet a further object of the invention to provide a method for calculating the distance between consecutive, retained data samples for use in constructing the sampled waveform;

It is a further object of the invention to provide a method for calculating the distance between consecutive, retained data samples for use in constructing the sampled waveform, wherein the distance between consecutive, retained data samples is calculated to describes a sample frequency that is less than the frequency of the input waveform;

It is yet another object of the invention to provide a method for compressing data samples that includes an amplitude companding mechanism; and It is another object to provide a system and method that can provide improved data compression capabilities while being implemented in hardware, software, or a combination thereof.

Other objects of the inventive system and method are described in the following specification and claims.

Summary of the Invention

These and other objects of the present invention are realized in improved turning point system and method for performing data compression. The system improves the conventional turning point compression method by selecting a predetermined number of the "best" turning points included in the sample window framed by data samples $X_0$ and $X_N$, wherein the framed data samples include $X_1, X_2 \ldots X_{(N-1)}$. From this sample window, ones of the data samples $X_1$ through $X_{(N-1)}$ will be identified as turning points using a selected one of the turning point detection methods discussed below. Using the turning point detection information, a predetermined number of samples are selected for retention. These samples may represent the best turning points based on a first predetermined set of criteria. If no turning points are detected, these samples are selected using a second predetermined set of criteria. The samples selected for retention are then stored. After selection of the retained samples, $X_0$ is set to the value of the most recently-retained data sample, $X_1$ is set to the value of $X_N$, and the process is repeated.

As noted above, several mechanisms may be use to determine which data samples are considered turning points. In one embodiment, a data sample is considered to be a turning point if the slopes of the two lines interconnecting that data sample with the two adjacent data samples change polarity. For example, if the line interconnecting $X_0$ and $X_1$ has a positive slope, whereas the line interconnecting $X_1$ and $X_2$ has a negative slope (or vice versa), $X_1$ is considered a turning point. Thus, in this instance, a turning point represents a peak or a valley in a waveform. In an alternative embodiment, a turning point may also include those points wherein a line having a non-zero slope intersects with a line having a zero slope. These turning points represent points wherein a "plateau" in a waveform meets a rising or falling portion of a waveform.

In yet a third embodiment, a turning point is defined as a point at which the waveform transitions from a generally "uphill" topology to a generally "downhill" topology, or vice versa. For example, consider a data sample window framed by data points $X_0$ through $X_N$ with $X_M$ being a data point somewhere between data points $X_0$ through $X_N$. Assume that the slopes of the lines drawn between consecutive pairs of data points between $X_0$ through $X_M$ are all either positive or zero. This waveform segment between points $X_0$ and $X_M$ therefore represents a generally upward trend in the waveform. At $X_M$, the waveform takes a downward turn, such that the slope of the line between data points $X_M$ and the next consecutive data point $X_{(M+1)}$ is negative. Since this negative, non-zero slope has a different polarity then the last non-zero slope that was encountered, $X_M$ is considered a turning point.

According to one mechanism, amplitude thresholding is used to determine whether a detected turning point should be retained. If the difference between the amplitudes of consecutive data points $X_M$ and $X_{(M+1)}$ is less than a predetermined threshold value, then $X_{(M+1)}$ may be eliminated as a turning point even if that point meets other pre-selected criteria. This mechanism removes from consideration small-amplitude turning points that are likely the result of noise. In one embodiment, the threshold value may be programmable so that turning point retention may be adapted to the noise level.

Once all turning points are identified within sample window $X_0$ through $X_N$, the current invention selects the "best" of these turning points for retention. Several selection mechanisms are available for selecting the "best" turning points. According to one embodiment of the invention, the sample window includes data samples $X_0$ through $X_3$, and the best turning point is determined by measuring which of the "unshared legs" of the waveform segment being considered is the largest. The unshared legs include a first line interconnecting $X_0$ and $X_1$, and a second line interconnecting $X_2$ and $X_3$. As between $X_1$ and $X_2$, the data point that is included within the segment having the largest change in amplitude is retained. It may be noted that this embodiment may retain a first data point over a second data point even in some situations in which the second data point is associated with a higher amplitude than the first data point. This is so because this criterion is not based upon absolute amplitude, but rather the size of the change between adjacent data points. In general, this criterion will reliably select the R wave of a PQRST complex within an EGM waveform, and therefore provides better compression as compared to the prior art turning point mechanisms.

A second embodiment of the invention selects the "best" turning point by determining which of the turning points within the window $X_0$ through $X_N$ has the greatest signal amplitude compared to a reference value, which in the preferred embodiment is zero volts. Unlike the "largest unshared leg" mechanism of the foregoing paragraph, the best turning point in this instance is considered to be the turn having the greatest absolute amplitude, regardless of the size of the turn. Yet another embodiment selects as the best turning point that point which has an amplitude that differs the most from the amplitude of $X_0$. Still another embodiment retains the turning point that is more positive than the other. This may be used to process signals in which the higher-amplitude segments are of more interest than the low-amplitude signals. Another embodiment retains the one of two turning points that is less positive than the other, and may be employed to process signals in which the low-amplitude or negative segments are of the highest interest. In one embodiment of the invention, the selection criterion is programmably-selectable based on the data set being processed.

It may be noted that more than one turning point may be retained per sample window. In this instance, many combinations of criteria may be devised to select the points to retain. For example, assuming two points are to be retained per frame, the two most positive peaks may be retained. Alternatively, the largest positive peak and the largest negative peak may be retained. In yet another embodiment, a largest positive peak value and the point representing the largest difference from $X_0$ may be retained. Many different combinations may be defined, and any number P data samples may be retained wherein P is less than N. This provides a compression ratio of (N–1)-to-P when a sample window of N+1 data samples is used.

In some embodiments, the compression ratio may be variable. This allows a variable number of data samples within a given sample window to be retained depending on the number of turning points detected within the window. For example, if the frequency of the input signal is high such that a relatively large number of the data samples within the sample window are turning points, a larger-than-average number of data samples may be retained for that sample window. A smaller-than-average number of data samples may be stored during another sample window. This may occur, for example, in a window in which no turning points are detected. Since it is desirable to have the average number of samples retained per sample window approach some predetermined target average value, a count of the number of "excess" data points that have been retained as compared to the target average is maintained. When this excess count exceeds a predetermined threshold value, the number of data points that may be retained during subsequent sample windows is temporarily reduced until the average number of saved data points per frame once again approximates the predetermined target average.

In embodiments in which the compression ratio varies depending on the input frequency, it may be desirable to save position data. This position data indicates the distance between consecutive data points such that waveform re-construction can be performed in a more accurate manner. This position data may precisely indicate the distance between retained data points. Alternatively, the position data may give an approximate distance between two points. For example, in one implementation, the position data indicates how many one-half sample windows exist between two retained sample points. According to this implementation, the position data only provides information at one-half of the input frequency of the sample data, such that some data is lost during this calculation. As a result, waveform re-construction cannot be performed with one hundred percent accuracy. However, this mechanism has the advantage of providing compacted position data that consumes less memory space.

In one implementation of the invention, position data may be stored in the same addressable storage location as a respective one of the retained sample. Alternatively, this position data may be stored in a different addressable storage location.

Another aspect of the invention relates to amplitude companding. The amplitudes of retained data samples may be scaled by a predetermined scaling factor so that less memory is required to store the samples. For example, an eight-bit digital data sample may be companded to six bits by dividing the data sample value by a factor of four. In another implementation, different scaling factors are used depending on the amplitude of the sample. High-amplitude and low-amplitude samples may be scaled more than mid-range signals, which are of interest when detecting the P-waves of an EGM signal, for example. Amplitude companding may be useful when position data is to be stored within a retained data sample. For example, an eight-bit data sample may be companded to six bits and stored in the same addressable memory byte with a respective two-bit position indicator. Other combinations of position data and signal data are, of course, possible.

The current turning point system and method may be cascaded to provide additional data compression. This cascading may be performed either serially or in parallel. For example, a two-to-one compression method may be applied to a data set twice to achieve four-to-one compression. Applying the method once again to the data set achieves eight-to-one data compression, and so on.

The system of the current embodiment may be implemented entirely in electronic circuitry using discrete devices, application specification integrated circuits, or other components in a manner know in the art. Alternatively, the invention may be implemented using a processor circuit under the control of software and/or firmware. A combination of specialized circuitry and programmed logic may also be utilized to implement the invention. Other aspects and embodiments of the current invention will become apparent from the description and accompanying drawings.

BRIEF DESCRIPTION OF THE DRAWINGS

FIG. 4 is a timing diagram of a QRS complex as may appear in an EGM signal, and illustrates application of the "largest unshared leg" embodiment of the best turning point system;

DETAILED DESCRIPTION OF THE PREFERRED EMBODIMENTS OF THE INVENTION

System of the Preferred Embodiment

Figure 1:
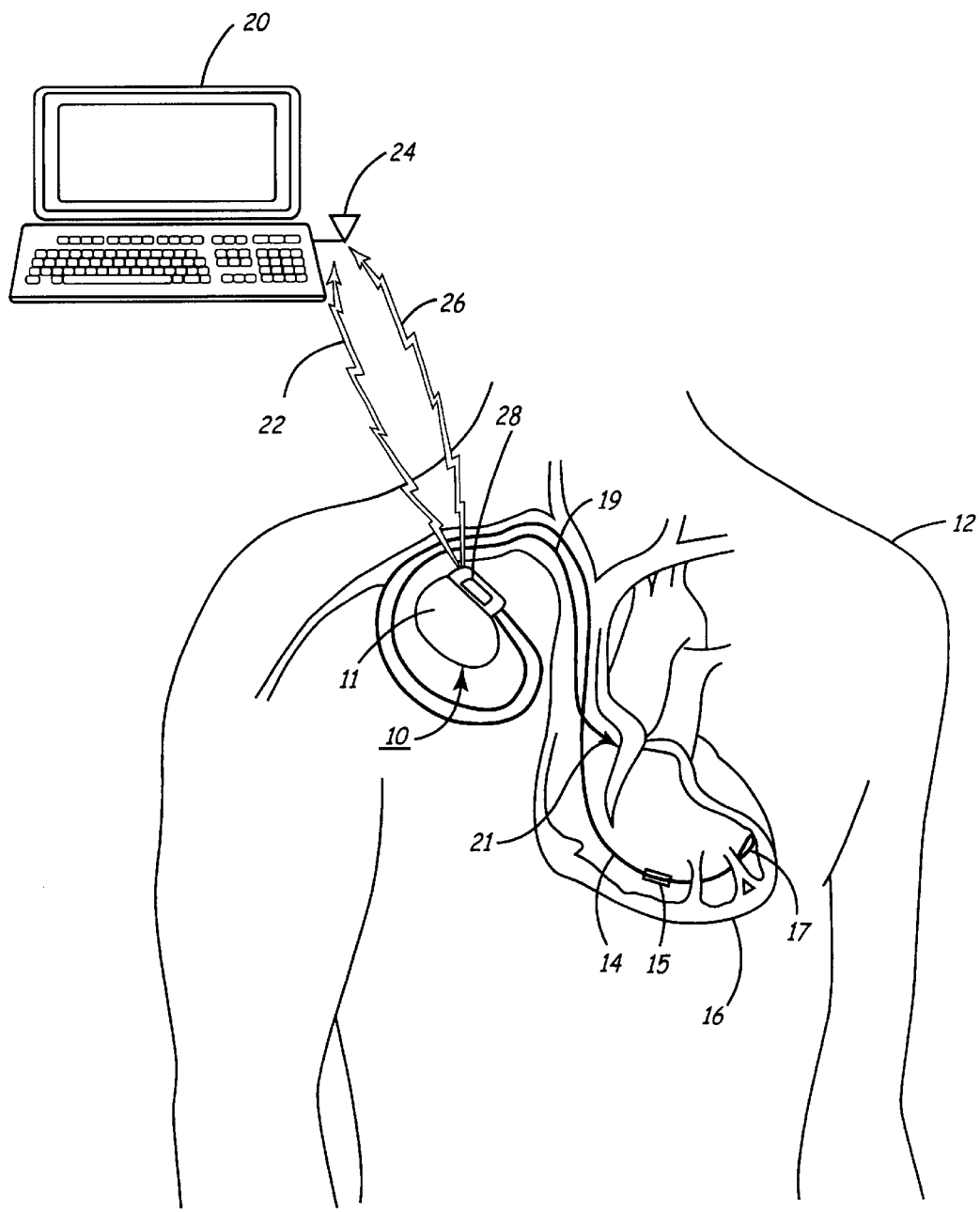
FIG. 1 is a schematic diagram illustrating an exemplary Implantable Medical Device (IMD) implanted within a patient and an associated device used to program the IMD via telemetry.

FIG. 1 is a schematic diagram illustrating an exemplary Implantable Medical Device (IMD) implanted within a patient. Also shown is an associated device used to program the IMD via telemetry. This IMD could be a pacing device, a defibrillation device, an implantable loop recorder, a hemodynamic monitor that does not provide a pacing therapy, or any other implantable cardiac therapy delivery device known in the art. In this example, the IMD is a cardiac pacemaker shown as IPG 10 implanted in the patient 12. The IPG 10 is electrically coupled to the heart 16 of the patient 12 through pace/sense electrodes and lead conductor (s) of at least one cardiac pacing lead 19 in a manner known in the art.

The LPG 10 contains an operating system that may employ a microcomputer or a digital state machine for timing sensing and pacing functions in accordance with a programmed operating mode. The IPG 10 also contains sense amplifiers for detecting cardiac signals, patient activity sensors or other physiologic sensors for sensing the need for cardiac output, and pulse generating output circuits for delivering pacing pulses to at least one heart chamber of the heart 16 under control of the operating system in a manner well known in the prior art. The operating system includes a storage device for storing operating parameters and other operating history data. The storage device may also be used for storing sensed physiological signals including those associated with cardiac activity.

Data signals stored by the LPG are transmitted between an IPG RF telemetry antenna 28 and an external RF telemetry antenna 24 associated with the external programmer 20. In an uplink telemetry transmission 22, the external RF telemetry antenna 24 operates as a telemetry receiver antenna, and the EPG RF telemetry antenna 28 operates as a telemetry transmitter antenna. Conversely, in a downlink telemetry transmission 26, the external RF telemetry antenna 24 operates as a telemetry transmitter antenna, and the IPG RF telemetry antenna 28 operates as a telemetry receiver antenna. Both RF telemetry antennas 24 and 28 are coupled to a transceiver including a transmitter and a receiver.

Atrial and ventricular pace/sense electrodes 21 and 17 are located at the distal ends of the atrial and ventricular leads 19 and 14, respectively. These leads are positioned in the right atrium and right ventricle, respectively. The electrodes 21 and 17 are shown as unipolar electrodes that are each paired with the conductive housing of the IPG 10 for unipolar pacing and far-field sensing. Alternative, bipolar electrode pairs may be provided at the distal ends of the atrial and ventricular leads 19 and 14, respectively, for bipolar pacing and near-field sensing. It will also be understood that the leads and pace/sense electrodes may be located in other locations than those depicted in FIG. 1. A blood pressure or other physiologic sensor 15 such as a pressure sensor is also shown provided on the ventricular lead body within the right ventricle.

Figure 2:
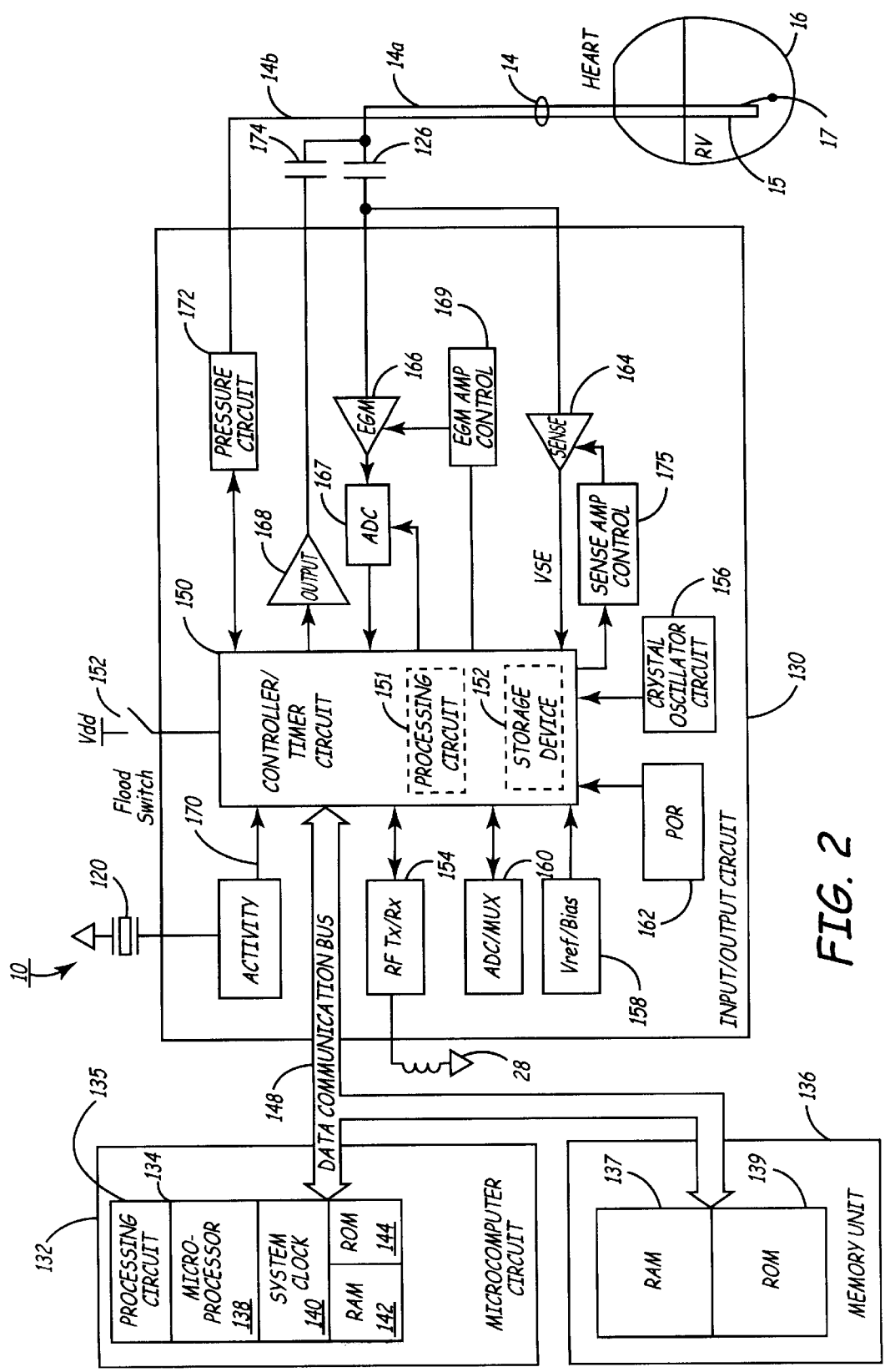
FIG. 2 is a circuit block diagram of an IMD.

FIG. 2 is a circuit block diagram of IPG 10. Only ventricular lead 14 and the ventricular pacing and sensing channel is depicted, although it will be understood that the atrial pacing and sensing channel is implemented in substantially the same manner.

IPG 10 includes input/output circuit 130. This circuit contains the analog circuits for processing cardiac signals, and any other signals such as those provided by activity sensor 120 and sensor 15 of lead 14. Input/output circuit 130 further receives the downlink RF telemetry signals received by RF telemetry antenna 28, as well as providing any pacing pulses to heart 16.

As discussed in reference FIG. 1, lead 14 includes an electrode placed in the vicinity of heart 16. Lead 14 includes lead conductors 14a and 14b. Lead conductor 14a is coupled via capacitor 126 to sense amplifier 164. The sense amplifier 164 is of conventional design and includes an amplification stage, a peak sense stage, and a threshold measurement stage. Controller/timer circuit 150 controls the gain of amplifier 164 via sensitivity control circuit 175.

Sense amplifier 164 provides a Ventricular Sense Event (VSE) signal indicative of cardiac activity to controller/timer circuit 150. The digital controller/timer circuit 150 employs programmed detection criteria to process the VSE signal. In response to this signal, the control/timer circuit may reset the pacing escape interval, trigger sense event markers, or make a determination of a malignant high heart rate.

Lead conductor 14a is further coupled to output pulse generator 168 through coupling capacitor 174. Output pulse generator 168 provides pacing pulses to the heart 16 in response to a pacing trigger signal developed by digital controller/timer circuit 150. The pacing trigger signal may be generated each time the escape interval elapses, or when an externally-transmitted pacing command has been received. The trigger signal may also be provided in response to other stored commands as is well known in the pacing art.

Lead conductor 14a is also coupled to EGM amplifier 166. This amplifier may be selectively activated via EGM amplifier control 169 to provide sampled waveform data to Analog-to-Digital Converter (ADC) circuit 167. In the preferred embodiment, EGM amplifier includes a 2-pole low pass filter with a cut-off at 100 Hz to remove high frequency noise. It further includes a single pole high pass filter at 2 Hz to remove baseline drift. The amplifier exhibits a linear phase over the frequency range of approximately 0 to 60 Hz.

ADC circuit 167 receives the filtered, amplified signal, which is generally sampled at 256 or 128 Hz. Sampling the EGM signal at 256 Hz is usually adequate to avoid aliasing because there is very little energy above 60 Hz included in the sampled signal. The sampled data may then be transferred to programmer 20 via the RF telemetry antenna 28 during real time uplink telemetry. This is as described in commonly-assigned U.S. Pat. No. 4,556,063, incorporated herein by reference in its entirety.

Lead conductor 14b extends from sensor 15, which in this example is a pressure sensor, to a pressure signal processing circuit 172 of the type described in the above-incorporated '040, '434, and '752 patents. Pressure signal processing circuit 172 receives, amplifies, and processes a signal received from sensor 15, and in turn, provides a signal indicative of cardiac pressure to controller/timer circuit 150. Controller/timer circuit 150 obtains a digital representation of the peak value of intracardiac pressure during each cardiac cycle. This value may be provided to microprocessor 134, which may maintain a running average pulse pressure calculated over a predetermined number of cardiac cycles. This value may be stored with the compressed EGM signal data for correlation therewith.

Input/output circuit 130 is coupled through a data communications bus 148 and control lines (not shown) to a microcomputer circuit 132. Microcomputer circuit includes a microprocessor 138, a system clock circuit 140, and on-board RAM 142 and ROM 144. Microprocessor provides the controller/timer circuit 150 with commands for controlling the timing of IPG 10. These commands establish the overall pacing escape interval, as well as various refractory, blanking, and other timing windows for controlling the operation of the peripheral components within input/output circuit 130.

In addition to controlling the pacing, sensing, and other functional aspects of the fPG, microprocessor 138 may also performing the data compression functions of the system. According to the current invention, microprocessor 138 may operate in conjunction with software or firmware loaded in either RAM 142, ROM 144, or the memory unit 136 to provide the data compression capabilities that are described herein. Memory unit 136 may include both RAM 137 and/or ROM 139. Alternatively, data compression capabilities could be implemented in circuitry shown simply as processing circuit 135. This circuitry could be any type of application-specific integrated circuitry, discrete components, or any combination thereof. The compression capabilities will be described in detail below.

As discussed above, data communications bus 148 is further coupled to an off-board memory unit 136 that could include RAM, ROM or both for storing both data, programming instructions, and any other operation parameters that may be needed by the system.

Input/output circuit 130 may further be coupled to activity sensor 120. This may be a piezoelectric element bonded to the inside of the housing of the IPG, or may be another type of activity sensor. Activity sensor 120 provides a signal indicative of patient activity levels to activity signal processor 170, which, in turn, provides a signal to controller/timer circuit 150. Controller/timer circuit 150 responds to this signal by adjusting the pacing rate to meet the metabolic requirements of the patient in a manner well known in the art.

The RF telemetry antenna 28 is coupled to controller/timer circuit 150 via RF transmitter/receiver 154 for purposes of performing uplink/downlink telemetry. Both analog and digital data may be transferred between antenna 28 and antenna 24 of FIG. 1. An uplink telemetry transmission of real time and stored data may be initiated when programmer 20 provides an interrogation command to IPG 10. Telemetry transmissions may be accomplished by employing any of the RF telemetry encoding schemes known in the art.

A reed switch 152 is also coupled to the digital controller/timer circuit 150. The reed switch 152 may be placed in a predetermined position upon the creation of a magnetic field in the vicinity of the implanted IPG. The switch position may be employed to alter the operating mode of IPG 10, or to enable uplink and downlink telemetry in a manner well known in the art.

Several other circuits are shown coupled to digital controller/timer circuit 150. A crystal oscillator circuit 156, which may operate at 32 Mhz, provides clock signals to controller/timer circuit 150. A Vref/Bias circuit 158 generates a stable voltage reference and bias currents for the analog circuits of input/output circuit 130. An analog-to-digital converter/multiplexor (ADC/MUX) unit 160 digitizes analog signals and voltages for storage in RAM, and may provide "real-time" telemetry of pressure and intracardiac signals.

ADC/MUX may also provide the battery End-Of-Life (EOL) replacement function. A Power-On-Reset (POR) circuit 162 provides reset circuitry to cause IMD to enter a default condition upon detection of a low battery condition, as will occur upon device power-up, or as may occur in the presence of electromagnetic interference.

Controller/timer circuit 150 may further include a processing circuit such as that shown as processing circuit 151, and may also include a storage device such as that shown as storage device 153. Processing circuit 151 could be any type of application-specific integrated circuitry, discrete components, or any combination thereof. This circuitry could be used alone or in conjunction with storage device to facilitate the data compression functionality of the current invention. This will be discussed in detail below.

After signals sensed by electrodes 21 and/or 17 are converted to a digital format, they may be provided by digital controller timer circuit via data communication bus 148 to microcomputer circuit 132. These signals may be stored in either the on-board RAM 142 or in memory unit 136. The storage of an EGM signal can be triggered by closure of the reed switch 152 when a magnet is positioned in the vicinity of this switch. This may be done upon the on-set of arrhythmia symptoms as is well known in the art. Within a defibrillation system, data storage may also be triggered upon entering a charging cycle as occurs in preparation for delivery of a cardioversion/defibrillation shock.

Either after, or prior to, the storage of a signal, the sampled data may be compressed. Compression may be performed either by microprocessor 138 or by a specialized circuit such as that shown as processing circuitry 135. Alternatively, compression may be performed by controller/timer circuit as mentioned above. The manner in which this compression is performed is described in detail in the following section.

The Turning Point Data Compression Method

As discussed above, one process for compressing data signals involves the use of the turning point mechanism. As stated previously, this method determines which of two consecutive samples of a waveform, $X_1$ or $X_2$, will be retained. To make this determination, the slope of the line between $X_1$ and $X_2$ is calculated. Additionally, the slope of the line between $X_1$ and $X_0$ is calculated, wherein $X_0$ is the last data point that was retained by the process. If one of these slopes is positive and the other slope is negative such that the product of these slopes is negative, $X_1$ is said to be a "turning point". That is, $X_1$ represents a "valley" or a "peak" in the sampled waveform. If $X_1$ is found to be a turning point, $X_1$ is retained. Otherwise, $X_2$ is retained. The retained data point is then considered to be $X_0$ and the data point not retained is discarded. The process is repeated using the next two sampled data points.

Figure 3:
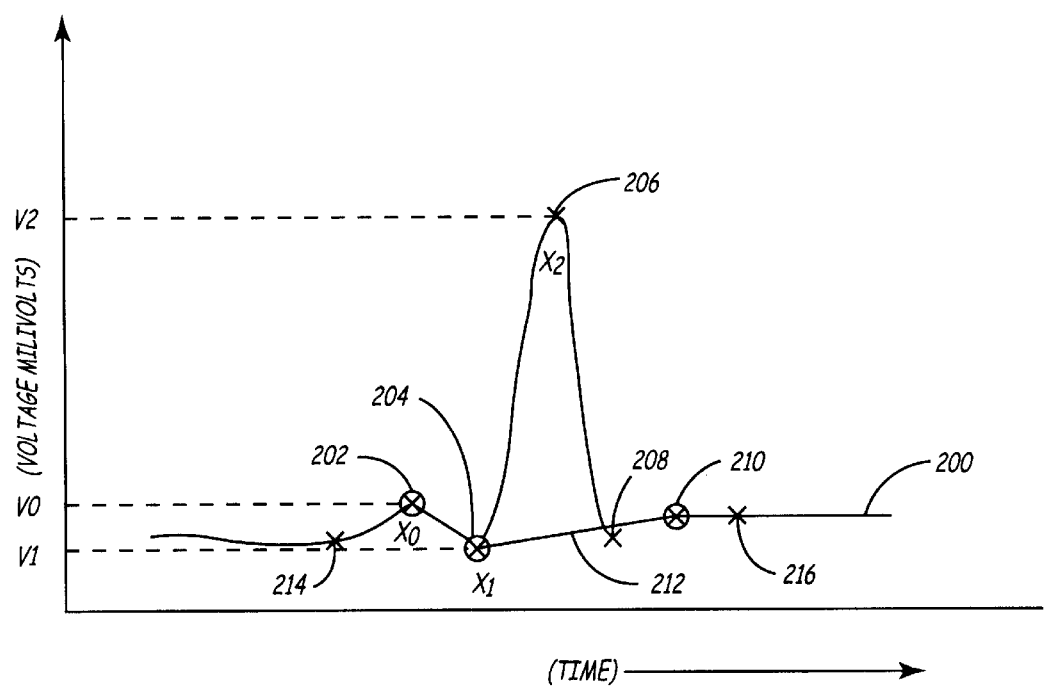
FIG. 3 is a timing diagram of a QRS complex of the type associated with an EGM signal, and illustrates the problem associated with the turning point compression method.

Mathematically, the turning point mechanism can be described using the amplitudes of the sample points, which are shown as voltage measurements in the waveforms discussed in the following paragraphs. For example, FIG. 3 shows the amplitudes of samples $X_0$, $X_1$, and $X_2$ as $V_0$, $V_1$, and $V_2$, respectively.

The mathematical representative of the turning point process could be expressed as follows:

If $(V_2-V_0)*(V_1-V_0)<0$, $X_1$ is a turning point. Therefore retain $X_1$, otherwise retain $X_2$.

It may be noted that although the above equation does not utilize actual slope calculations that take into account both x-axis and y-axis components, the equation detects the change in polarity of two slopes, and is therefore adequate for turning point detection. Other methods of detecting a turning point are discussed above in reference to the current invention.

Problems exist when the above method is applied to a waveform having two turning points that are in close proximity to one another. If both $X_1$ and $X_2$ represent turning points of a waveform, and $X_2$ is a more important turning point than $X_1$, $X_2$ will never-the-less be discarded because $X_1$ is always retained when $X_1$ is a turning point. When the waveform is reconstructed using the compressed data, significant distortion results.

FIG. 3 is a timing diagram of a QRS complex of the type associated with an EGM signal, and illustrates the problem associated with the turning point compression method. Samples are being taken at predetermined, regular time intervals represented on the X axis. Signal amplitude, which in this example is a signal voltage measured in millivolts (mvs) is measured on the y-axis. Sample $X_0$ is shown as data point 202. Samples $X_1$ and $X_2$ are shown as data points 204 and 206, respectively. It is readily appreciated that a line between $X_0$ and $X_1$ has a negative slope, whereas a line between $X_1$ and $X_2$ has a positive slope. The equation $$(V_2-V_1)*(V_1-V_0)<0$$

is therefore true. $X_1$ is a turning point shown as a "valley" of waveform 200, and $X_1$ is retained. $X_2$ will be discarded.

During the next iteration of the process, the retained data point 204 is considered to be $X_0$, and data points 208 and 210 are considered to be $X_1$ and $X_2$, respectively. The variables $V_0$-$V_2$ are the voltage measurements at the new sample points $X_0$-$X_2$, respectively. In this case, it will be assumed the slope between data points 204 and 208, which are the new $X_0$ and $X_1$, respectively, is zero. Therefore, the equation $$(V_2-V_1)*(V_1-V_0)<0$$

is false since the new $V_0$ and $V_1$ (not shown in FIG. 3) are the same. Therefore $X_2$, which is data point 210, is retained instead of $X_1$. The string of retained data points for this segment of the waveform includes data points 202, 204, and 210. The reconstructed waveform shown as waveform segment 212 illustrates the distortion created by application of the turning point algorithm to the QRS complex. The entire R wave has been eliminated from the reconstructed data.

It may be further noted that the turning point algorithm is dependent on which sample point is selected as $X_0$ during the first iteration of the process. For example, assume that sample point 214, rather than sample point 202, is considered to be $X_0$ in the first iteration that is discussed above. Application of the turning point mechanism to data points 202 through 210 in the manner discussed above would, in this case, result in the retention of data points 214, 202, and 206 rather than retention of data points 262, 204, and 210. Upon de-compression, the resulting waveform would be very different from that illustrated by waveform segment 212. For the foregoing reasons, an improved turning point method and apparatus is desired.

The Improved Turning Point Process

In contrast to prior turning point methods, the new turning point system and method described herein makes a determination as to whether both $X_1$ and $X_2$ are turning points. This is accomplished using an extra data point $X_3$, which is the data point following $X_2$ in the sample stream. As discussed above, a determination as to whether $X_1$ is a turning point may be made using the polarity of the slopes of the lines between $X_0$ and $X_1$, and between $X_1$ and $X_2$. Similarly, it is determined whether $X_2$ is a turning point using the polarity of the slopes of the lines between $X_1$ and $X_2$, and between $X_2$ and $X_3$.

If it is determined that both $X_1$ and $X_2$ are turning points, the current invention provides superior data compression by retaining the "best" turning point. The best turning point may be selected using one of several embodiments of Applicants' invention. According to a first embodiment, the "unshared" legs of the portion of the waveform in question are used to determine the best turning point. This is best illustrated by considering FIG. 4.

Figure 4:
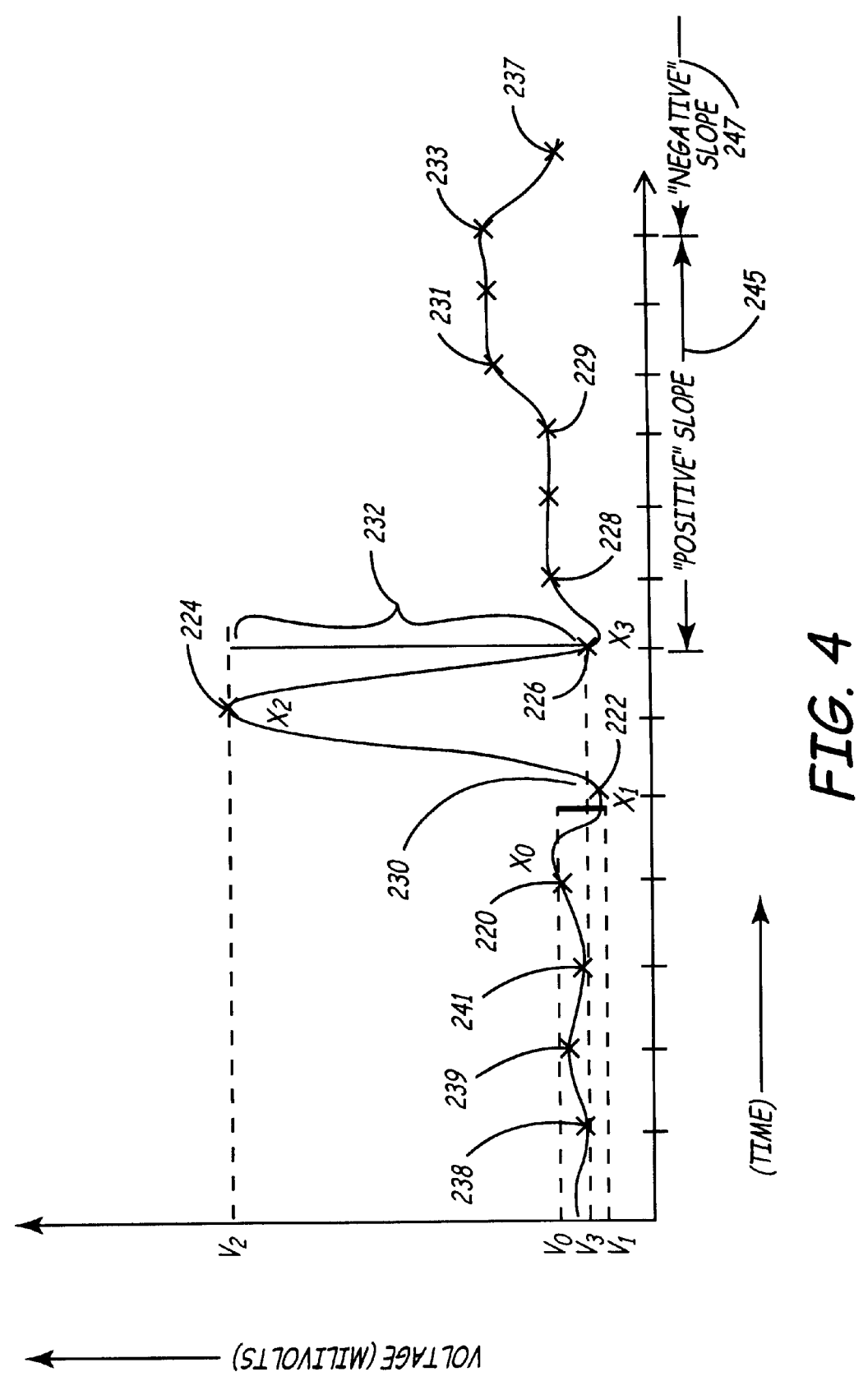

FIG. 4 is a timing diagram of a QRS complex as may appear in an EGM signal, and illustrates application of the "largest unshared leg" embodiment of the best turning point system. In this example, data points 220, 222, 224, and 226 will be considered $X_0$, $X_1$, $X_2$, and $X_3$, respectively. According to this embodiment, a comparison is made between the waveform segment between $X_0$ and $X_1$, and the waveform segment between $X_2$ and $X_3$. More specifically, the difference between the waveform amplitude (which in this instance is a voltage measurement) at point $X_2$ and the amplitude at point $X_3$ is calculated. This difference may be represented by line 232. Additionally, the difference between the voltage at point $X_0$ and the voltage at point $X_1$ is calculated, as represented by line 230. The largest of these two differences determines the largest unshared leg. In this case, line 232 is larger than line 230, and the segment between $X_2$ and $X_3$ is the largest unshared leg. Therefore $X_2$ is retained whereas $X_1$ is discarded.

Mathematically, the largest unshared leg criterion can be expressed as follows:

IF $\{[|(V_3-V_2)|<|(V_1-V_0)|]\}$ AND $[(V_1-V_0)(V_2-V_1)<0]$ AND $[(V_3-V_2)(V_2-V_1)<0]$}

THEN retain $X_1$, otherwise retain $X_2$.

In the above equation, the variables $V_0$ through $V_3$ represent the voltage amplitudes of data points $X_0$ through $X_3$, respectively, as shown in FIG. 4. Three clauses are presented. Since "AND" is used as the connector between clauses, each of the clauses must be true for $X_1$ to be selected. The second clause is true if $X_1$ is a turning point. The third clause is true if $X_2$ is a turning point. The first clause is true when the absolute difference between the amplitudes of $X_0$ and $X_1$ is greater than that difference between $X_2$ and $X_3$. Thus, $X_1$ is retained when both $X_1$ and $X_2$ are turning points, and $X_1$ is the turning point that is included within the largest unshared leg. Otherwise $X_2$ is retained.

When applying the above criterion to samples $X_1$ and $X_2$ of FIG. 4, $X_2$ will be retained instead of $X_1$. Thus, the R wave is retained using this improved mechanism, whereas the R wave is discarded using the previous turning point process.

It will be noted that the above-discussed criterion is intended to address the situation in which both $X_1$ and $X_2$ are turning points. Since this is not always the case, some criterion is needed to select between $X_1$ and $X_2$ when only one, or neither, of the data points are turning points. One criterion that may be used is provided by the following statement:

IF {$[(V_1-V_0)(V_2-V_1)<0]$ AND $[(V_3-V_2)(V_2-V_1)>0)]$}, THEN retain $X_1$, otherwise retain $X_2$.

This criterion retains $X_1$ when $X_1$ is a turning point (as determined by the first clause of the statement) AND when $X_2$ is not a turning point (as determined by the second clause of the statement). $X_2$ will be retained when neither $X_1$ nor $X_2$ are turning points, or when just $X_2$ is a turning point.

The above two criteria may be combined to provide the following data compression mechanism:

IF either of the following Case I or Case II is true:

{$[(V_1-V_0)(V_2-V_1)<0]$ AND $[(V_3-V_2)(V_2-V_1)>0)]$}  (CASE I)

OR

{$[|(V_3-V_2)|<|(V_1-V_0)|]$ AND $[(V_1-V_0)(V_2-V_1)<0]$ AND $[(V_3-V_2)(V_2-V_1)<0]$}  (CASE II)

then retain $X_1$, otherwise, retain $X_2$.

As previously discussed, Case I selects $X_1$ when $X_1$ is the only turning point. Case II selects $X_1$ when both $X_1$ and $X_2$ are turning points, and $X_1$ is the "best" turning point as determined by the "largest unshared leg" criterion discussed in reference to FIG. 4. $X_2$ is retained when $X_2$ is the only turning point, when $X_2$ is the best turning point, or when neither $X_1$ nor $X_2$ are turning points.

When the above method is applied to the waveform of FIG. 3 using the sample points illustrated, it will be appreciated that $X_2$ is retained instead of $X_1$, since $X_2$ is part of the largest unshared leg. This improved turning point mechanism therefore provides superior data compression characteristics as compared to the prior art method while still providing a system that is not processing-intensive.

Alternative Methods of Detecting a Turning Point

The best turning point method discussed above detects a turning point by detecting whether the slopes of the lines drawn between a selected point and the two points on either side of the selected point change polarity. That is, $X_1$ is a turning point if the line between $X_0$ and $X_1$ has a positive slope and the line between $X_1$ and $X_2$ has a negative slope, or vice versa, and may be referred to as the "peak/valley method". This situation is detected when a product of the slopes is less than zero. That is, $X_1$ is a turning point if $(V_2-V_1)(V_1-V_0)<0$. This method detects turning points that are at the very peak or valley of a waveform.

An alternative method may be employed to detect as turning points those points at which a rising or falling slope meet a plateau, and may be referred to as the "plateau-detect method". This type of data point is exemplified by data point 228 of FIG. 4. To detect this situation, a criterion like the following can be used:

$[(V_2-V_1)(V_1-V_0)$ LE $0]$ AND {$[(V_2-V_1)\neq 0]$ OR $[(V_1-V_2)\neq 0]$}

In this instance, if the product of the slopes is Less-than, or Equal to (LE), zero, and either one of the slopes is not equal to zero, the point is considered a turning point.

One problem with the foregoing approach is that it detects the "steps" in a generally upward or downward waveform segment. In FIG. 4, for example, this method detects all of points 228, 229, and 231 as turning points. All of these points are associated with a waveform segment between data samples 226 and 233 having a generally "uphill" topology. Therefore, points 228, 229, and 231 may not be as important to retain as some other samples. For example, at data point 233, the slope changes from one that is generally positive (or zero) to one that is negative. Therefore, data sample 233 may be considered of more importance than points 228–231.

To detect only the turning points of greater importance, the polarity of the last non-zero slope value is saved during the processing of consecutive waveform segments. For example, during the processing of data points 226 and 228, a "positive" indication is save. This value remains saved throughout the processing of data point 233, since between samples 226 and 233, no waveform segments are located with slopes that are anything other than "positive" or "zero". This is shown by arrow 245. However, during the processing of data points 233 and 237, a waveform segment with a non-zero, negative slope is detected. Since the polarity of the slope is not equal to the saved polarity value of "positive", the data point 233 is detected as a true turning point, and the new saved non-zero slope value is set to "negative", as shown by arrow 247. According to this method, which may be referred to as the "slope-difference method", only data points 226 and 233 are detected as turning points, whereas points 228, 229 and 231 are not. This alternative method of detecting data points will be discussed further below.

Yet another alternative mechanism for detecting a turning point is to disregard turns that are of relatively small amplitude. Returning to FIG. 4, consider data points 238, 239, and 241. This portion of the signal waveform could result from sixty-hertz noise, for example. To prevent each of these data points from being detected as a turning point, a minimum threshold could be applied to the difference between signal amplitudes of adjacent data points. For example, if the difference in amplitudes of adjacent data points is less than a predetermined amplitude such as one mV, the data point is not considered a turning point. As can be seen from FIG. 4, such a threshold could be used to prevent data points 238, 239 and 241 from being detected as turning points.

For ease of reference, all of the alternative "best turning point" methods that are discussed in the following sections are shown to use the turning point detection mechanism that was first described herein. That is, the examples show the simplified mechanism of detecting a peak or valley in the waveform. However, it will be understood that any one of the alternative turning point detection mechanisms discussed in the foregoing paragraphs may be used instead. Still other types of turning point detection mechanisms may be employed as well.

Alternative Methods of Handling Sample Windows With No Turning Points

In the above example, $X_2$ is retained when no turning points are included in a particular sample window, regardless of the relationship of $X_1$ and $X_2$. This method is simple to implement, and retains the data point that will often exhibit the greatest amplitude difference as compared to the last retained point. An alternative method may be employed if it is desirable to always retain the point with the maximum amplitude deviation from the previous retained point when no turning points are detected within a sample window. This improvement could be expressed as follows:

IF $\{[(V_0-V_1)(V_1-V_2)>0]$ AND $[(V_3-V_2)(V_2-V_1)>0)]$ AND $[|V_2-V_0|<|V_1-V_0|]\}$, THEN retain $X_1$, otherwise retain $X_2$.

One skilled in the art will appreciate that adding this statement as an additional Case II to the above-discussed turning point mechanism, along with the addition of appropriate modifications to the Case I statement, will ensure that the data point with maximum amplitude deviation from a previous retained point will be selected in a sample window having no detected turning points. This will hereinafter be referred to as the "no-turning-point, highest-deviation" criterion.

Alternative Methods of Determining the Best Turning Point

Other methods may be used to determine which of two consecutive turning points should be retained as the best turning point. For example, one alternative embodiment employs a "largest turn detector" to determine which of two samples $X_1$ and $X_2$ is retained. According to this criterion, the data point having an amplitude with the greatest absolute different from a predetermined reference signal level is the point retained.

Figure 5:
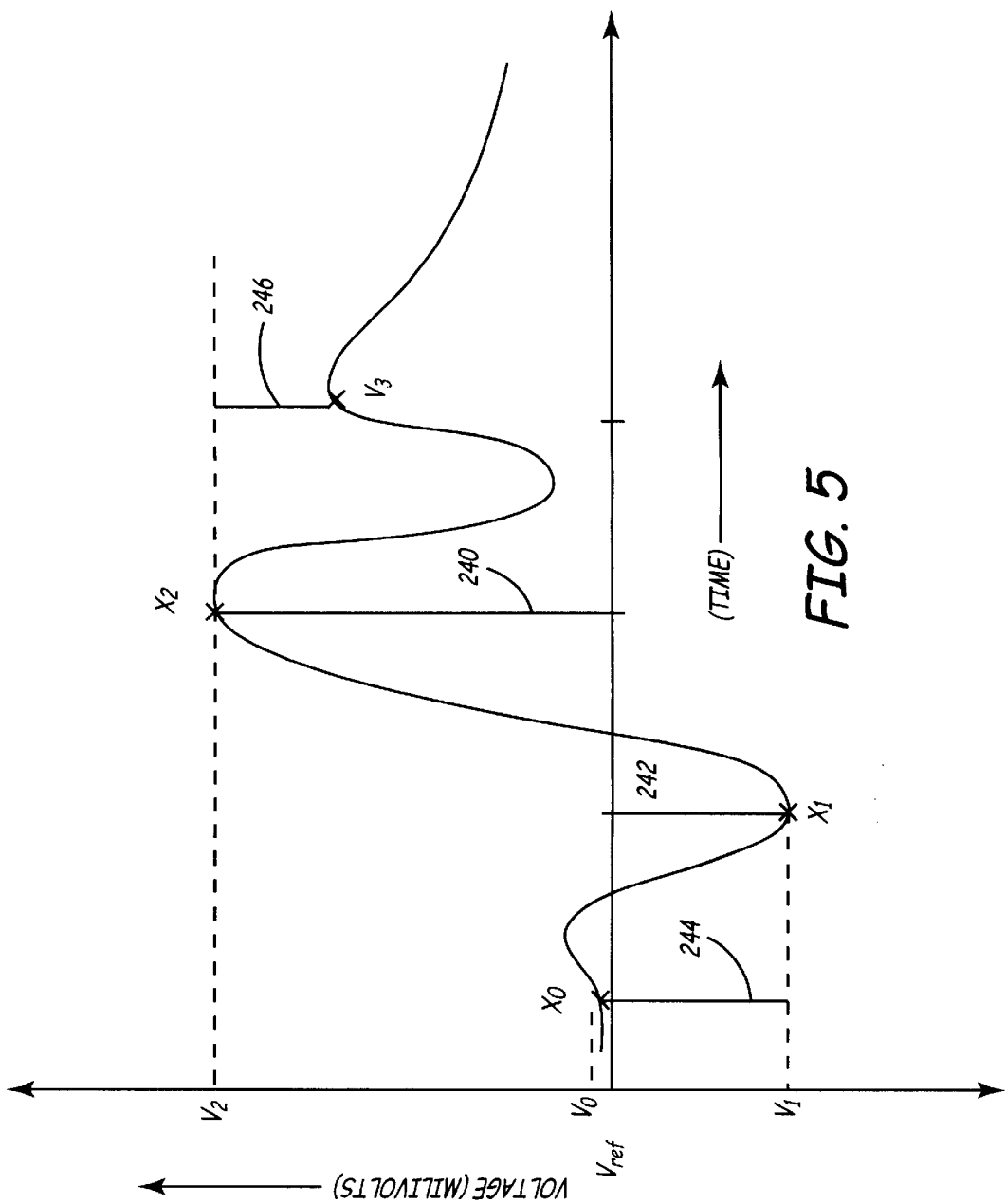
FIG. 5 is a timing diagram of a QRS complex, and illustrates the use of the largest turn detector criterion for selecting between two consecutive sampled data points $X_1$ and $X_2$.

FIG. 5 is a timing diagram of a QRS complex, and illustrates the use of the largest turn detector criterion for selecting between two consecutive sampled data points $X_1$ and $X_2$. As in the above examples, the signal amplitude is expressed in millivolts. The reference voltage $V_{ref}$ is determined by the voltage measurement at the intersection of the X and Y axis. This reference voltage could be selected as "zero" or some other arbitrary reference voltage point. Line 240 represents the difference between the voltage measurement at $X_2$ and the reference voltage $V_{ref}$. Similarly, line 242 represents the difference between the voltage measure at $X_1$ and the reference voltage $V_{ref}$. Since the difference represented by line 240 is clearly larger than the difference represented by line 242, this criterion selects $X_2$ as the data point for retention.

Mathematically, this selection criterion may be expressed as follows:

IF $\{[|(V_2-V_{ref})|<|(V_1-V_{ref})|]$ AND $[(V_1-V_0)(V_2-V_1)<0]$ AND $[(V_3-V_2)(V_2-V_1)<0]\}$, then retain $X_1$, otherwise retain $X_2$.

That is, if $X_1$ and $X_2$ are both turning points, and the difference between $V_{ref}$ and the voltage at point $X_1$ is greater than the difference between $V_{ref}$ and the voltage at point $X_2$, retain $X_1$, otherwise retain $X_2$.

If $V_{ref}$ is set to 0, this equation can be re-stated as follows:

IF $\{[|V_2|<|V_1|]$ AND $[(V-V_0)(V_2-V_1)<0]$ AND $[(V_3-V_2)(V_2-V_1)<0]\}$, then retain $X_1$, otherwise retain $X_2$.

It may be noted that if the largest unshared leg criterion discussed above were applied to the data of FIG. 5, $X_1$ would be retained instead of $X_2$. This is because the absolute value of the difference between the voltage measurements at $X_0$ and $X_1$, which is displayed by line 244, is larger than the absolute value of the difference between the voltages measured at $X_2$ and $X_3$, as displayed by line 246. This illustrates that in some instances, it may be desirable to match the appropriate improved turning point criterion to the cardiac condition being analysed, since the criterion selected may change the data the is retained. This will be discussed further below.

In the same manner as discussed above in reference to the "largest unshared leg" criterion, a complete representation of the "largest turn" criterion may be expressed mathematically as follows:

IF either of the following Case I or Case II is true:

$\{[(V_1-V_0)(V_2-V_1)<0$ AND $[(V_3-V_2)(V_2-V_1)>0)]\}$   (CASE I)

OR $\{[|(V_2-V_{ref})|<|(V-V_{ref})|]$ AND $[(V_1-V_0)(V_2-V_1)<0]$ AND $[(V_3-V_2)(V_2-V_1)<0]\}$ (CASE II)

then retain $X_1$, otherwise, retain $X_2$.

As discussed above, Case I is used to evaluate the situation in which $X_1$ and $X_2$ are not both turning points. Case I selects $X_1$ when $X_1$ is the only turning point. Case II selects $X_1$ when $X_1$ is the best turning point as determined using the "largest turn" criterion. $X_2$ is selected when $X_2$ is the only turning point, when $X_2$ is the best turning point as determined using the "largest turn" criterion, or when neither $X_1$ nor $X_2$ are turning points.

When this method is applied to the waveform of FIG. 3, it will be appreciated that $X_2$ is retained instead of $X_1$, since $X_2$ is part of the largest turn. Thus, in a manner similar to that discussed above in reference to the largest unshared leg embodiment, this embodiment of the invention provides superior data compression characteristics as compared to the prior art system and method.

Yet another embodiment of the best turning point process of the present invention involves the use of a criterion referred to as the "largest change from $X_0$". According to this criterion, when both $X_1$ and $X_2$ represent turning points, the best turning point is the one in which the signal amplitude differs the most from the amplitude at point $X_0$.

Figure 6:
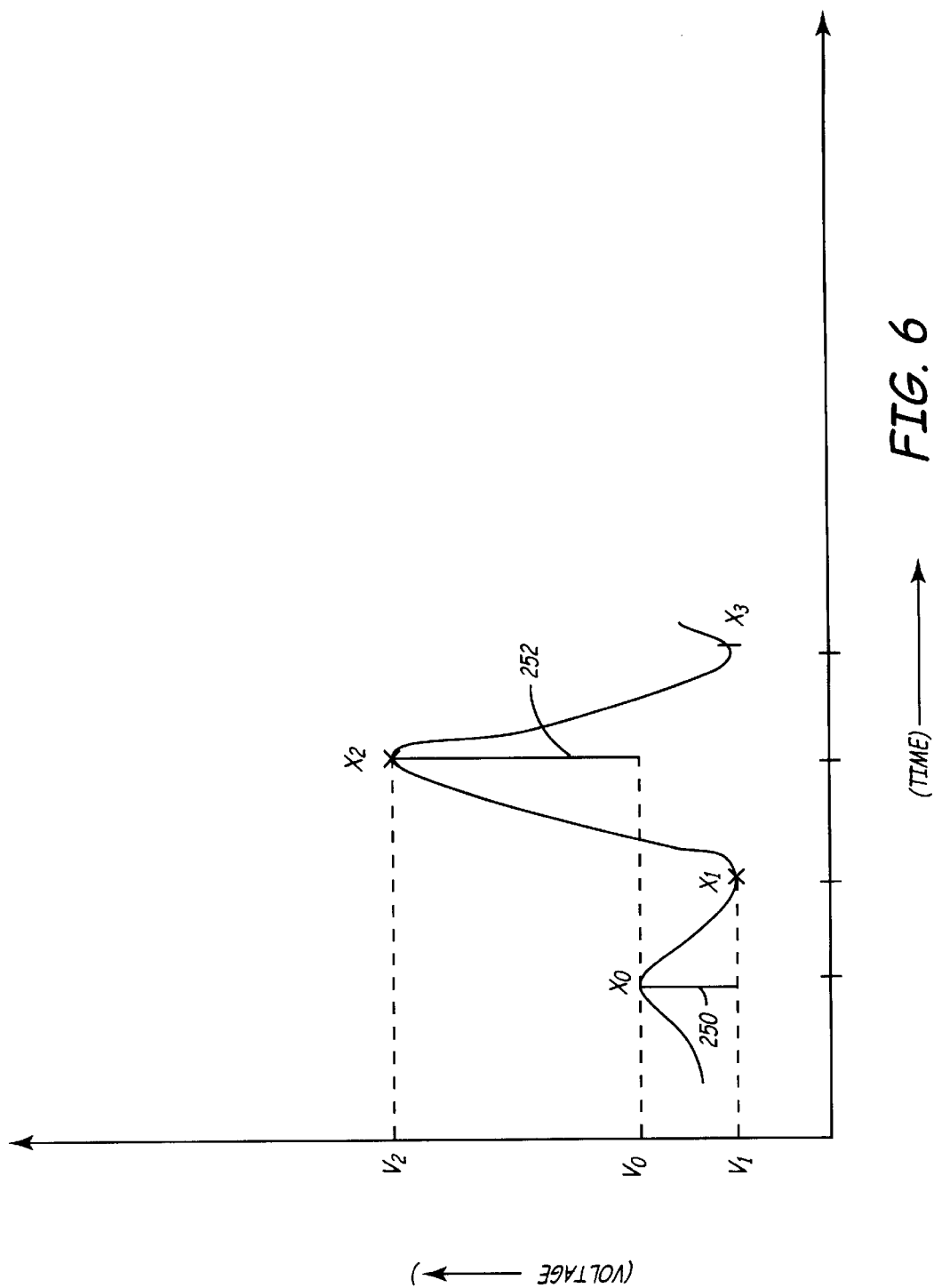
FIG. 6 is a timing diagram of a QRS complex, and illustrates the use of the "largest change from $X_0$" criterion for selecting between two consecutive sampled data points $X_1$ and $X_2$.

FIG. 6 is a timing diagram of a QRS complex, and illustrates the use of the "largest change from $X_0$" criterion for selecting between two consecutive sampled data points $X_1$ and $X_2$. Line 250 represents the difference between the amplitudes at points $X_0$ and $X_1$, which in this example is signal voltage, but which could be another type of measurement. Line 252 represents the difference between the amplitudes at points $X_0$ and $X_2$. Using this criterion, $X_2$ is selected as the data point to be retained since line 252 is clearly longer than line 250.

Mathematically, the "largest change from $X_0$" mechanism may be described as follows:

IF either of the following Case I or Case II is true:

$\{[(V_1-V_0)(V_2-V_1)<0]$ AND $[(V_3-V_2)(V_2-V_1)>0)]\}$   (CASE I)

OR $$\{[|(V_2-V_0)|<|(V_1-V_0)|] \text{ AND } [(V_1-V_0)(V_2-V_1)<0] \text{ AND } [(V_3-V_2)(V_2-V_1)<0]\} \quad \text{(CASE II)}$$

then retain $X_1$, otherwise, retain $X_2$.

In a manner similar to that discussed, Case I selects $X_1$ when $X_1$ is the only turning point. Case II selects $X_1$ when $X_1$ is the best turning point as determined using the "greatest change from $X_0$" criterion. This is determined using the first clause of the Case II statement. $X_2$ is retained over $X_1$ when $X_2$ is the only turning point, when $X_2$ is the best turning point as determined using the "greatest change from $X_0$" criterion, or when neither $X_1$ nor $X_2$ are turning points. When this method is applied to data points of the waveform of FIG. 3, $X_2$ is retained instead of $X_1$, since the difference between the voltage measurements at $X_2$ and $X_0$ is larger than the difference between the voltage measurements at $X_1$ and $X_0$. Thus, this embodiment again may be used to provide superior data compression characteristics as compared to the prior art system and method.

It may be noted once again that the use of this criterion may result in the retention of different data points as compared to the alternative criteria discussed above in reference to FIGS. 4 and 5. This may be illustrated by FIG. 7.

Figure 7:
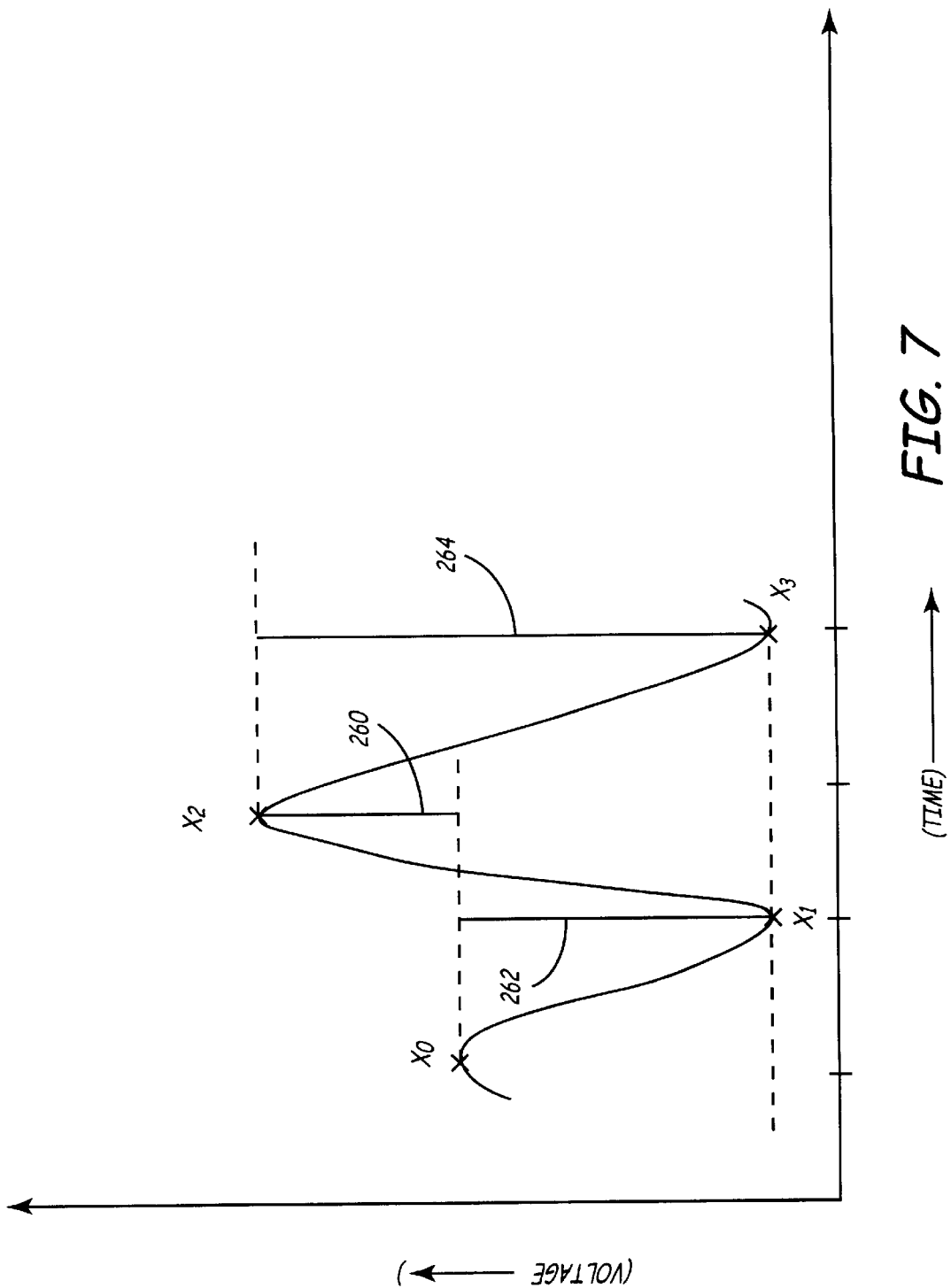
FIG. 7 is a timing diagram of a QRS complex, and compares the use of the "largest change from $X_0$" criterion with the "largest unshared leg" criterion.

FIG. 7 is a timing diagram of a QRS complex, and compares the use of the "largest change from $X_0$" criterion with the "largest unshared leg" criterion. When applying the "largest change from $X_0$" criterion to data points $X_0$, $X_1$, and $X_2$, data point $X_1$ is retained. This is illustrated by comparing line 260, which represents the difference between the voltage amplitudes at points $X_0$ and $X_1$, with line 262, which represents the difference between the voltages at points $X_0$ and $X_2$. Since the voltage difference is greater in the latter case, $X_1$ is retained.

Next, the "largest unshared leg" criterion is applied to the data points of FIG. 7. In this case, line 262, which represents the difference between the voltages at points $X_0$ and $X_1$, is compared against the difference between the voltages at points $X_2$ and $X_3$, as represented by line 264. In this case, the voltage difference represented by line 264 is greater than that represented by line 262, and $X_2$ is therefore retained. This again illustrates that it may be desirable to select a particular embodiment of the current invention that is optimal for a particular data set. This will be discussed further below.

Still another embodiment of the best turning point system and method uses the "largest positive peak" criterion to select a data point to retain. According to this criterion, when both $X_1$ and $X_2$ represent turning points, the best turning point is considered to be the one associated with the "most positive" peak. This could be useful when the primary concern is the missing of R waves in an EGM signal. This method could be described as follows:

IF either of the following Case I or Case II is true:

$$\{[(V_1-V_0)(V_2-V_1)<0] \text{ AND } [(V_3-V_2)(V_2-V_1)>0]\} \quad \text{(CASE I)}$$

OR $$\{[V_2<V_1] \text{ AND } [(V_1-V_0)(V_2-V_1)<0] \text{ AND } [(V_3-V_2)(V_2-V_1)<0]\} \quad \text{(CASE II)}$$

then retain $X_1$, otherwise, retain $X_2$.

Case I selects $X_1$ when $X_1$ is the only turning point. Case II selects $X_1$ when both $X_1$ and $X_2$ are turning points and the amplitude at $X_1$ is greater (more positive) than that at $X_2$. Thus, in this case, the best turning point is the most positive turning point. As stated previously, this ensures the retention of R-waves when the current compression mechanism is applied to EGM data points. $X_2$ is retained when $X_2$ is the only turning point, when $X_2$ is greater than, or equal to, $X_1$, or when neither $X_1$ nor $X_2$ are turning points. When applied to data points $X_1$ and $X_2$ of FIG. 3, this process will retain $X_2$ since $V_2$ is more positive than $V_1$.

In a different embodiment, the retention of the least positive turning points may be more desirable than retention of the most positive turning points. In those instances, the improved turning point process could be described as follows:

IF either of the following Case I or Case II is true:

$$\{[(V_1-V_0)(V_2-V1_1)<0] \text{ AND } [(V_3-V_2)(V_2-V_1)>0)]\} \quad \text{(CASE I)}$$

OR $$\{[V_1<V_2] \text{ AND } [(V_1-V_0)(V_2-V_1)<0] \text{ AND } [(V_3-V_2)(V_2-V_1)<0]\} \quad \text{(CASE II)}$$

then retain $X_1$, otherwise, retain $X_2$.

Case I selects $X_1$ when $X_1$ is the only turning point. Case II selects $X_1$ when both $X_1$ and $X_2$ are turning points and $X_2$ is less than $X_1$. In this case, the best turning point is therefore the turning point that is the least positive. When applied to sample points $X_1$ and $X_2$ of FIG. 3, this mechanism will retain $X_1$ since $V_1$ is less positive than $V_2$.

Cascading

As mentioned previously, the improved turning point mechanism may be applied multiple times to the same data set in a cascaded fashion to achieve a higher compression ratio. For example, applying the improved turning point process to a data set once will achieve two-to-one data compression. The method may be applied to the compressed data set yet again to achieve four-to-one compression. Applying the method yet again will yield eight-to-one compression, and so on. The cascading can be applied in serial or in a more parallel manner as will be discussed below.

Best Turning Point Mechanism Using "N" Samples

For ease of explanation, each of the above examples utilizes a sample window containing four data points $X_0$–$X_3$, wherein a single data point is selected from samples $X_1$ and $X_2$ for retention, and data points $X_0$ and $X_3$ "frame" the sample window. This results in two-to-one data compression. The above mechanism could easily be adapted for use with a sample window containing N+1 data points $X_0$–$X_N$ wherein N+1 is greater than four. Using any of the turning point detection methods set forth above, the N+1 data points may be used to determine which of N+1 data points in the sample window are turning points. Once this determination is made, the best turning point may be selected using any of the best turning point criteria discussed above.

As an example of a best turning point mechanism using greater than a four-sample window, consider a sample window including the seven data samples $X_0$–$X_6$. Up to five turning points may be detected, since each of the samples $X_1$–$X_5$ may be a turning point. After the turning points have been identified, the single best turning point may be retained from among these samples. This may be accomplished, for example, by selecting the turning point representing the most positive peak. Any of the other best turning point criteria, such as the "largest unshared leg" criterion, may be applied to the turning points in a similar manner. This exemplary system will achieve a five-to-one compression ratio. One skilled in the art may readily adapt the mathematical criteria set forth above to accomplish this task.

In yet another embodiment of the current invention, more than one data point may be retained per sample window. For example, two data samples may be retained by the foregoing example having sample windows including $X_0$–$X_6$. This could be accomplished by retaining the two turning point with the largest peaks, for example. Alternatively, the two turning points representing the largest peak and largest unshared leg, respectively, could be retained (assuming these points are not the same). A second selection criterion could be used to select the second retained sample if the same point is both the largest peak and the largest unshared leg. One can easily appreciate that the set of possible criteria that may be devised to select a predetermined number of points from each sample window is very large, and if desired, can be tailored to match the characteristics of the data set being processed. This system would achieve a five-to-two data compression ratio.

System for Retaining a Variable Number of Data Points

Another embodiment of the current invention allows a variable number of data points to be retained within a sample window. The number of points retained could be determined by the frequency of the input waveform, for example. To illustrate, consider a sample window containing four data points $X_0$–$X_3$. As discussed above, assuming a single point is retained in each sample window, this type of system will achieve two-to-one compression. However, such a system may be allowed to retain both data points $X_1$ and $X_2$ when both samples are turning points. Such a system could thereafter "catch up" to the target two-to-one compression ratio by not saving any data points if a window is encountered without any turning points. One skilled in the art will appreciate that the foregoing system could readily be adapted for use with sample windows containing N+1 samples wherein N+1 is greater than four. Such systems may be further adapted to retain, on average, more than two turning points per window. The mathematical criteria discussed above may be readily modified to achieve the desired results.

Providing a system with a variable compression ratio improves the fidelity of the high frequency ranges of the reconstructed signal waveform. However, it creates additional challenges. For example, if some sample windows are associated with greater than the "normal" number of retained samples, and other sample windows are associated with fewer samples, it may be desirable to record positioning data along with the samples. The positioning data will indicate the relative position of a particular retained data point in reference to the last retained data point. However, storage of this positioning data consumes valuable memory resources and at least partially defeats the purpose of the data compression. Thus, some compromise must be reached in the amount of positioning data stored, and the amount of fidelity retained in the re-constructed waveform. In one preferred embodiment, a two-bit tag field is used to store an encoded value indicative of the distance between a current retained data point and the last retained data point. This is best shown by example.

Figure 8:
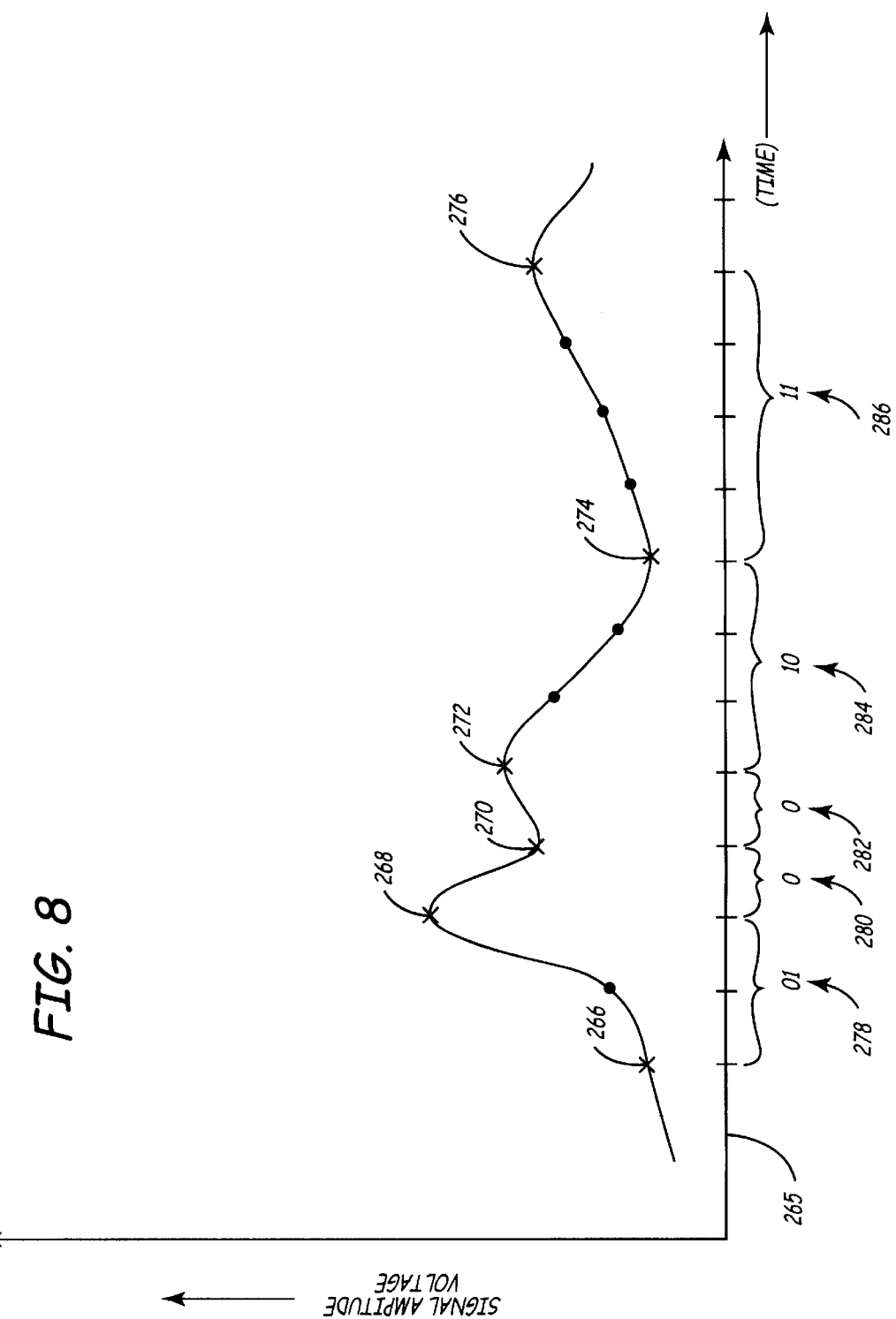
FIG. 8 is a waveform illustrating one manner in which position tags may be used within a system that utilizes a variable compression ratio.

FIG. 8 is a waveform illustrating one manner in which position tags may be used within a system that utilizes a variable compression ratio. In this example, sampling is performed at the intervals shown on the X axis 265. The retained turning point samples are shown as data points 266, 268, 270, 272, 274, and 276. The position tag 278 is associated with data point 268. The two-bit encoded binary value "01" is assigned to data point 268 as a position indicator since one sample is "skipped" from the last retained data point 266. The binary value "0" is assigned to data points 270 and 272 since no samples are skipped between data points in this case. This is shown by position tags 280 and 282, respectively. For data points 274 and 276, the position tags "10" 284 and "11" 286 are used, respectively, to indicate the appropriate number of skipped samples.

It may be noted that the size of the position tag field limits the number of samples that may be skipped. For example, even if data point 276 had not been a turning point, this point could not have been skipped since, at most, only three skipped samples can be indicated by the two-bit position tag.

The position tags of FIG. 8 provide an exact indication of the position of a retained sample within the data stream, and no position data is lost. In another embodiment, the position resolution is reduced to one-half of the input data rate such that some position data is lost. For example, consider a system in which sample windows include $X_0$–$X_5$, and data compression is performed on samples $X_1$–$X_4$ to achieve four-to-one compression. A position tag could be utilized to indicate in which half of the data frame a retained sample point resides. That is, both $X_1$ and $X_2$, if retained, would be associated with the same position tag. Likewise, both $X_3$ and $X_4$ would be associated with the same position tag. While the position tag will not indicate the exact location of the retained data point within the sample stream, it may be considered "close enough" since some distortion in the recreated waveform is considered acceptable. This allows more sample points to be skipped, if necessary, while minimizing the amount of storage needed for the position tag.

Figure 9:
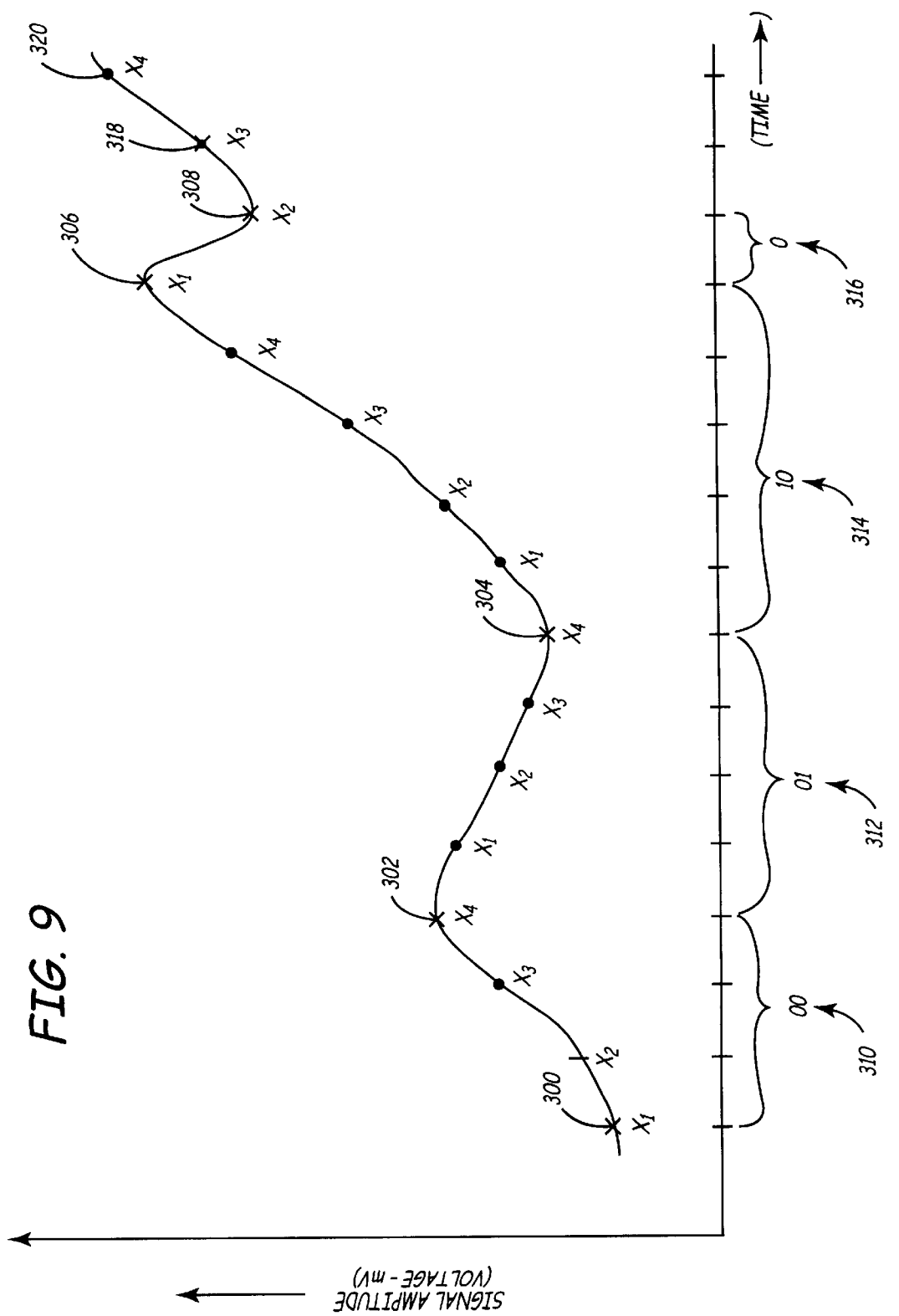
FIG. 9 is a waveform illustrating the use of position tags for recording position data at one-half the input frequency.

FIG. 9 is a waveform illustrating the use of position tags for recording position data at one-half the input frequency. This example corresponds to the system discussed in the preceding paragraph wherein four-to-one data compression is achieved by selecting between samples $X_1$–$X_4$, which are framed within a sample window including data points $X_0$–$X_5$. For purposes of this example, it will be assumed that, at most, two samples maybe retained for each sample window. In FIG. 9, the retained data points are shown as samples 300, 302, 304, 306, and 308.

The sampling rate is shown on the x axis. The position tag 310 associated with data point 302 indicates that zero half-frames have been skipped. This is so because data point 300 is in the first half-frame comprising points $X_1$ and $X_2$ of the sample window, whereas $X_4$ is in the second half-frame of the same sample window including $X_3$ and $X_4$. Therefore, no half-frames have been skipped. Data point 304 is associated with position tag 312, indicating that one half-frame has been skipped. This is because no data points associated with the preceding half-frame containing $X_1$ and $X_2$ were retained. Similarly, data point 306 is associated with position tag 314, indicating that two (binary "10") half-frames have been skipped. This is the case because none of the data points $X_1$–$X_4$ between data points 304 and 306 were retained.

Next, data point 308 is considered. This data point is associated with the same half-frame as data point 306. If data point 306 had not been retained, position tag 316 for data point 308 would be set to "10", indicating that two half-frames were skipped. This is the same value assigned to position tag 314 for data point 306. As stated previously, this is because $X_1$ and $X_2$ are in the same half-frame, and two half-frames separate both data points 306 and 308 from the last retained data point 304. However, since data point 306 is retained, data point 308 will effectively be moved into the next half-frame by assigning it a position tag of zero. The next two sample points $X_3$ and $X_4$, 318 and 320, respectively, will be discarded since the maximum number of two sample points have already been retained within the sample window.

Storing the Position Tag Fields

As stated previously, the position tag fields must be stored along with the retained sample data. One way to do this is to pack multiple position tags together in one storage location. For example, four one-byte retained data samples may be stored followed by a byte containing the four associated two-bit position tags associated with the preceding four data samples.

Figures 10, 11:
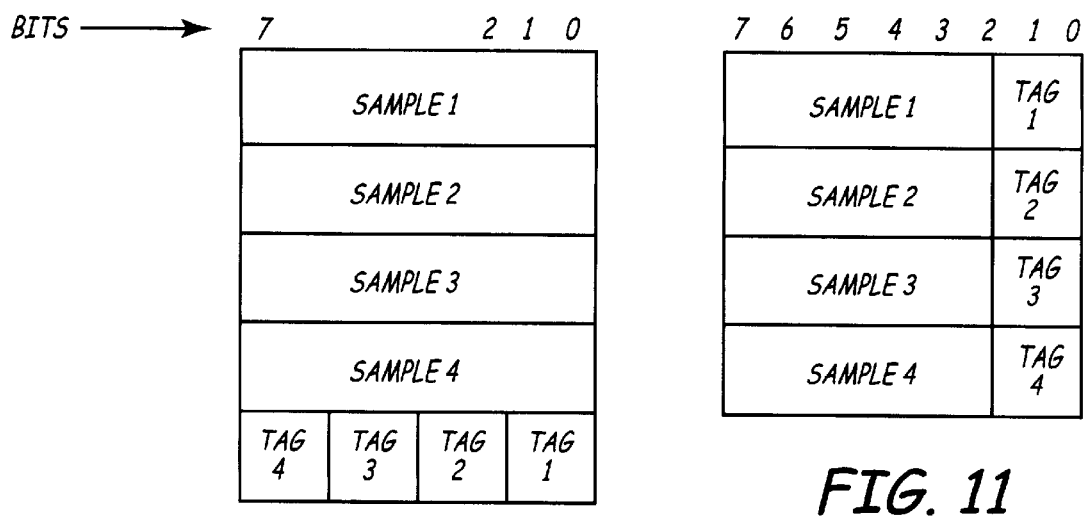
FIG. 10 is a block diagram illustrating the manner in which multiple position tags are stored within a single memory location.
FIG. 11 is a block diagram illustrating an alternative method of storing position tags with the associated data sample.

FIG. 10 is a block diagram illustrating the storing of multiple position tags within a single memory location. Samples one through four are stored in the four preceding bytes, with the respective position tags being stored in the following byte.

FIG. 11 is a block diagram illustrating an alternative method of storing position tags with the associated data sample. If each data sample were compressed from eight bits to six, the position tag field could be stored within the same eight-bit byte as the data sample. This would result in loss of some signal fidelity, but would also conserve storage space.

One manner of preforming data compression is to simply divide the signal value by four. That is, the least significant two bits of the eight-bit signal value are discarded. This results in loss of low-level signal detail, however. For example, the P-waves of EGM signals may be discarded because of this type of amplitude compression.

An alternative to the above-described compression function may be provided by a companding mechanism. This mechanism divides the possible range of amplitude values described by an eight-bit byte into ranges, wherein at least one range describes high-amplitude signals and another range is indicative of low amplitude signals. The high-amplitude signals are then compressed at a greater rate than low amplitude signals to preserve detail of the low-level signals. For example, within the possible amplitude range of −128 through 127 as provided by an eight-bit byte, signals within the range −32 to 31 are considered low amplitude and are only compressed by a factor of two. For signals outside of this range, the signal amplitude is compressed using a transfer function that takes into consideration the scale factor of the first range, in addition to a second larger scale factor such as a factor of six. More specifically, in the current example, the transfer function would be as follows:

| | |
|---|---|
| Companded Amplitude = Signal Amplitude/2 | If −31 < Signal Amplitude < 32 |
| Companded Amplitude = (Signal Amplitude − 32)/6 + 16 | If Signal Amplitude >= 32 |
| Companded Amplitude = (Signal Amplitude + 31)/6 − 17 | If Signal Amplitude <= −31 |

The above transfer function therefore scales the "portion" of the signal amplitude that is less-than, or equal to, "thirty-two" at the first scale factor of "two", while scaling the remainder of the signal amplitude at the second scale factor of "six".

An alternative companding method may be used to reduce noise. According to this mechanism, signals having an amplitude between −7 and +6 are reduced by a factor of three. Signal amplitudes outside this first range that are within the range of −34 to +33 are not companded at all to preserve details such as P-waves of an EGM signal. Finally, signals outside of the range of −34 to +33 may be scaled by a factor a six. In this example, a transfer function such as the following is used:

| | |
|---|---|
| Companded Amplitude = Signal Amplitude/3 | If −7 < Signal Amplitude < 6 |
| Companded Amplitude = Signal Amplitude | If 6 < Signal Amplitude < 33 OR If −34 < Signal Amplitude < −7 |
| Companded Amplitude = (Signal Amplitude − 33)/6 + 33 | If Signal Amplitude >= 33 |
| Companded Amplitude = (Signal Amplitude + 34)/6 − 34 | If Signal Amplitude <= −34 |

Figure 12:
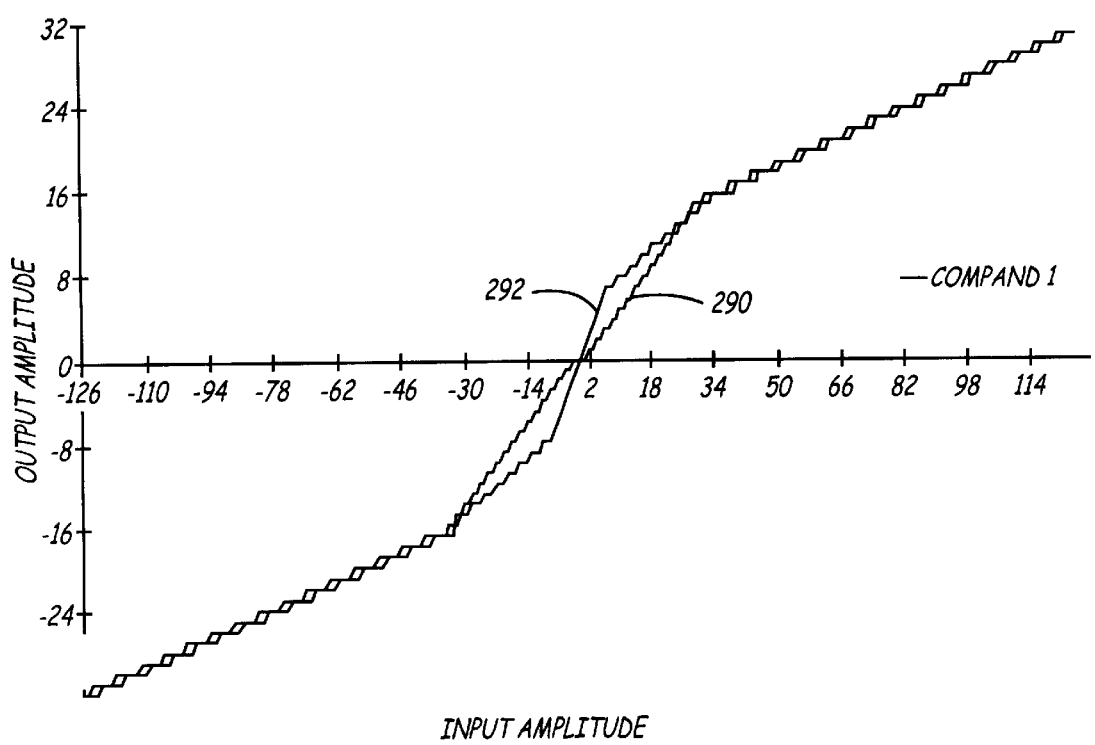
FIG. 12 is a diagram illustrating several exemplary amplitude companding transfer functions.

FIG. 12 is a diagram illustrating amplitude companding transfer functions of the above examples. The waveform 290 illustrates the two-range companding mechanism that does not include a range for reducing noise, as described in the preceding paragraph. Waveform 292 illustrates the three-range mechanism, including the mechanism for reducing low-level noise while retaining intermediate-level signal detail. It will be understood that the transfer functions of FIG. 12 are merely illustrative in nature, and any other transfer functions of this nature may be used instead, including functions using any additional number of defined signal amplitude ranges, each having a respective transfer function associated therewith.

As noted above, amplitude compression allows a position tag to be stored in the same eight-bit byte as the associated amplitude data. It may further be noted that in some systems associated with stored EGM waveform data, markers are inserted to indicate the occurrence of certain events. These markers are identified by tags having the values of 81 or 82 (hexidecimal) stored within the bytes preceding the markers. In systems using markers, it is important to store the position tags within the least significant bits of the byte such that a position tag is not mistaken for a marker tag.

The foregoing paragraphs discuss a system in which compression ratios vary as the frequency of the input waveform changes. Thus, multiple turning points may be retained within some sample windows whereas no data points are retained within other sample windows. When processing a waveform that includes many high-frequency signal intervals, this type of system may exhibit an overall compression ratio that is too low, and the amount of available memory may be insufficient to store the retained data points.

One way to ensure that a system attains a target compression ratio is to track the number of stored samples that are in excess of the target ratio. When this excess number of stored samples exceeds a predetermined threshold level, the storing of samples may be limited or prohibited altogether. This is best shown by example.

Consider a system having a sample window consisting of $X_0$–$X_5$, and which has a target compression ratio of four-to-one. Thus, on average, one data point should be retained each sample window to attain the target compression ratio. Further assume that this system allows for the retention of between zero and two data points per sample window depending on input signal frequency. To ensure that the target compression ratio is approximated, a count is maintained to track the number of retained data points that are in excess of the one-per-frame allowed average. In the current example, the count is initially set to zero before sampling is started. Assume that thereafter, three consecutive sample windows are encountered in which two data points are retained per window. During each of these three sampling windows, the count value is incremented by one to reflect the saving of the additional data point that is in excess of the one-per-frame target storage rate. Thus, after the processing of the three frames, the count records that three "excess" data points have been saved.

For the current example, it will be assumed that a threshold value of "two" has been selected to determine when the storing of data points is to be reduced. Since the count in this is instance has been incremented to "three" and now exceeds the threshold value, the number of data points that may be retained within a sample window is reduced to a smaller number, such as one sample per window.

The count will remain set to three as long as sample windows are encountered in which one data sample is stored. When a sample window is encountered in which no data samples are stored because no turning points are detected, the count is decremented by "one". Thereafter, the count value no longer exceeds the threshold value. Thus, the number of samples that may be stored per sample window is increased to the initial number, which is "two" in this example.

Figure 13:
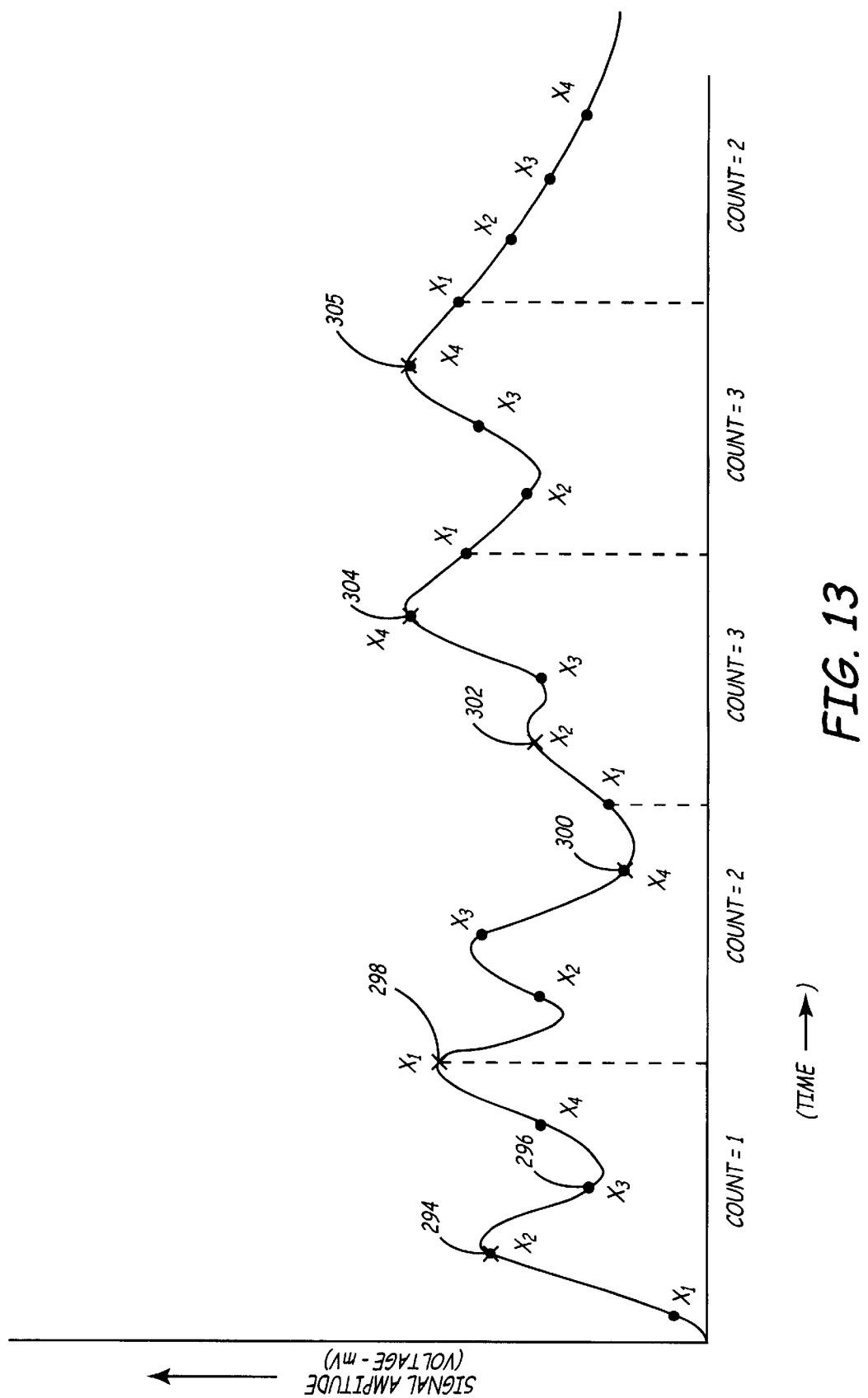
FIG. 13 is a timing diagram illustrating the use of threshold values to control the variable compression ratio in a manner discussed in the foregoing paragraph.

FIG. 13 is a timing diagram illustrating the use of threshold values to control the variable compression ratio in a manner discussed in the foregoing paragraphs. During each of the first three sample windows, two data points are retained. These retained samples are shown as data samples 294–304. This exceeds the target average compression ratio by one data point per frame. Therefore, the cumulative number of "excess" data points (shown as "count" in FIG. 13) increases by one during each of the first three sample windows. During the fourth sample window, the number of "excess" data points exceeds the threshold value, which is set to "two" in this example. Thus, only one of the turning points shown as turning point 305 is retained. The excess count remains set to "three". During the fifth sample window, no turning points are located, and no data points are retained. Therefore, the excess count value is decremented by one such that it no longer exceeds the threshold value. Thus, if necessary, two data points may be retained in the sixth sample window.

An almost infinite number of turn detection criteria may be used to implement the variable turning detection method discussed above. According to one preferred embodiment, a four-to-one data compression system is used in the manner discussed above. During each sample window, a frame of data points consisting of $X_0$–$X_5$ is considered. Turn detection is performed on each of the data points $X_1$–$X_4$. In the preferred embodiment, turns are detected using a mechanism that is insensitive to noise through the use of amplitude thresholding as discussed above. Moreover, only "true" turns are detected by using the above-described "slope-difference" method.

In the system of the preferred embodiment, the following rules are applied to determine the turning points to be retained:

If no turns are detected, the "no-turning-point, highest-deviation" criterion is applied, as discussed above.

If only a single turn is detected, the turn is retained.

If two turning points are detected, and the "excess count" value has not exceeded the threshold count, both turning points are retained.

If more than two turning points are detected, and the "excess count" value has not exceeded the threshold count, the two turning points having the most positive and least positive (most negative) amplitudes are retained.

If more than one turning point is detected, and the "excess count" value has exceeded the threshold count, the turning point having the largest deviation from the last retained point is retained.

As will be appreciated by one skilled in the art, the system and method described herein may be implemented in many ways. For example, the system shown in FIG. 2 could include circuitry that applies the best turning point mechanism to sampled EGM data points that have already been stored in one of the storage facilities of IPG 10. Alternatively, data compression could be applied to samples received in real-time from ADC circuit 167, or to data signals that are provided on data communication bus 148.

Figure 14:
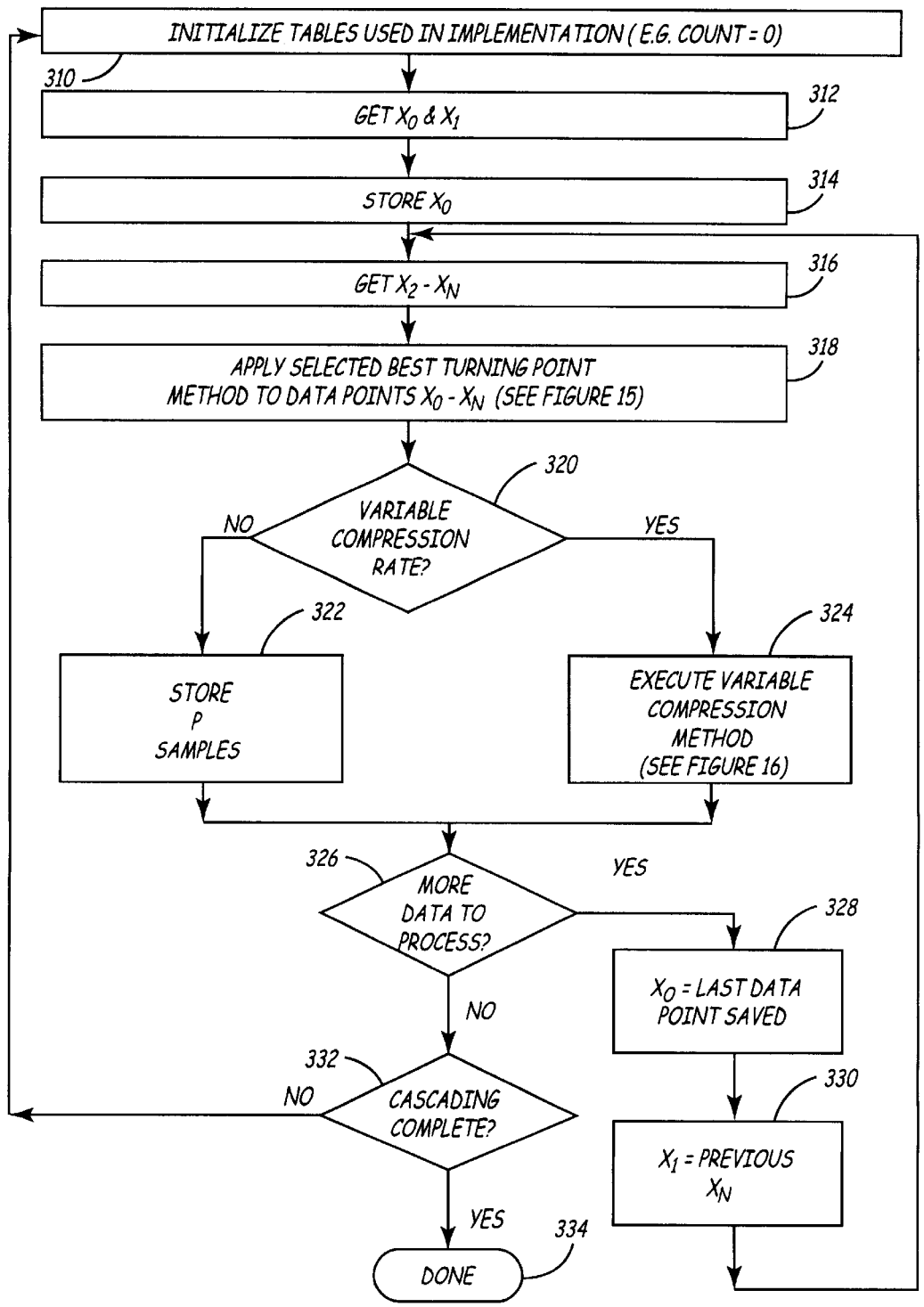
FIG. 14 is a flowchart illustrating the method employed by the current invention.

FIG. 14 is a flowchart illustrating the method employed by the current invention. In step 310, variables are initialised. The variables used will depend on the implementation employed, but might include a count value (shown as "Count") for use when variable compression rates are used in a manner to be discussed below. This variable is shown being initialized to zero. In Step 312, data points $X_0$ and $X_1$ are obtained. These samples may be obtained directly from the sampling circuit in real time, or may be retrieved from a storage device. Next, as shown in Step 314, data point $X_0$ is stored in some storage device such as RAM, or a bank of registers. Data points $X_2$–$X_N$ are retained next, as illustrated in Step 316. The number of data points used in a given sample window is variable, and depends on the specific implementation in a manner discussed above.

Step 318 shows the application of a selected best turning point method, which may include any of those discussed above, some combination thereof, or any variant thereof. The selected method will utilizes a window of N data points to determine whether any of the N–2 data points framed within the sample window are turning points. This is described in more detail in FIG. 15.

Decision Step 320 determines whether a variable compression rate may be employed. If not, execution continues with Step 322, which selects a predetermined number of samples P from among the best turning point(s) detected in Step 320 for storage. These selected data points may be stored in any storage device such as RAM, an array of Registers, or any other storage device. The number P is variable, and depends on the implementation in a manner discussed above.

If a variable compression rate is being employed, execution instead continues to Step 324 in which a method is executed to process the variable compression function. This is described in detail in FIG. 16.

After execution of either Steps 322 or 324, execution proceeds to Step 326, where it is determined if more data points remain to be processed. If so, $X_0$ is set to the most recent data point that was retained, and $X_1$ is set to the value of $X_N$ from the current iteration. This is shown in Steps 328 and 330, respectively. Processing then returns to Step 316 to obtain the next set of data points $X_2$–$X_N$. If, during the last iteration, all N data points are not available, some predetermined method could be used to "pad" the window, such as by filling it with samples having the same amplitudeas the last available data point.

Returning to decision Step 326, if no more data points remain to be processed, execution continues with decision Step 332 where it is determined if the desired number of compression iterations have been performed on the data such that cascading may be said to have been completed. This number of compression iterations may be programmably selected, if desired, by initializing a variable in Step 310 to indicate the number of times to perform the method. If cascading is not completed such that another iteration of the compression method is to be performed, processing continues with Step 310 wherein variables are reinitialized and execution is initiated again. If cascading is completed, either because multiple iterations of the method are not to be executed or because execution of all iterations is complete, processing is completed as shown by Step 334.

Figure 15:
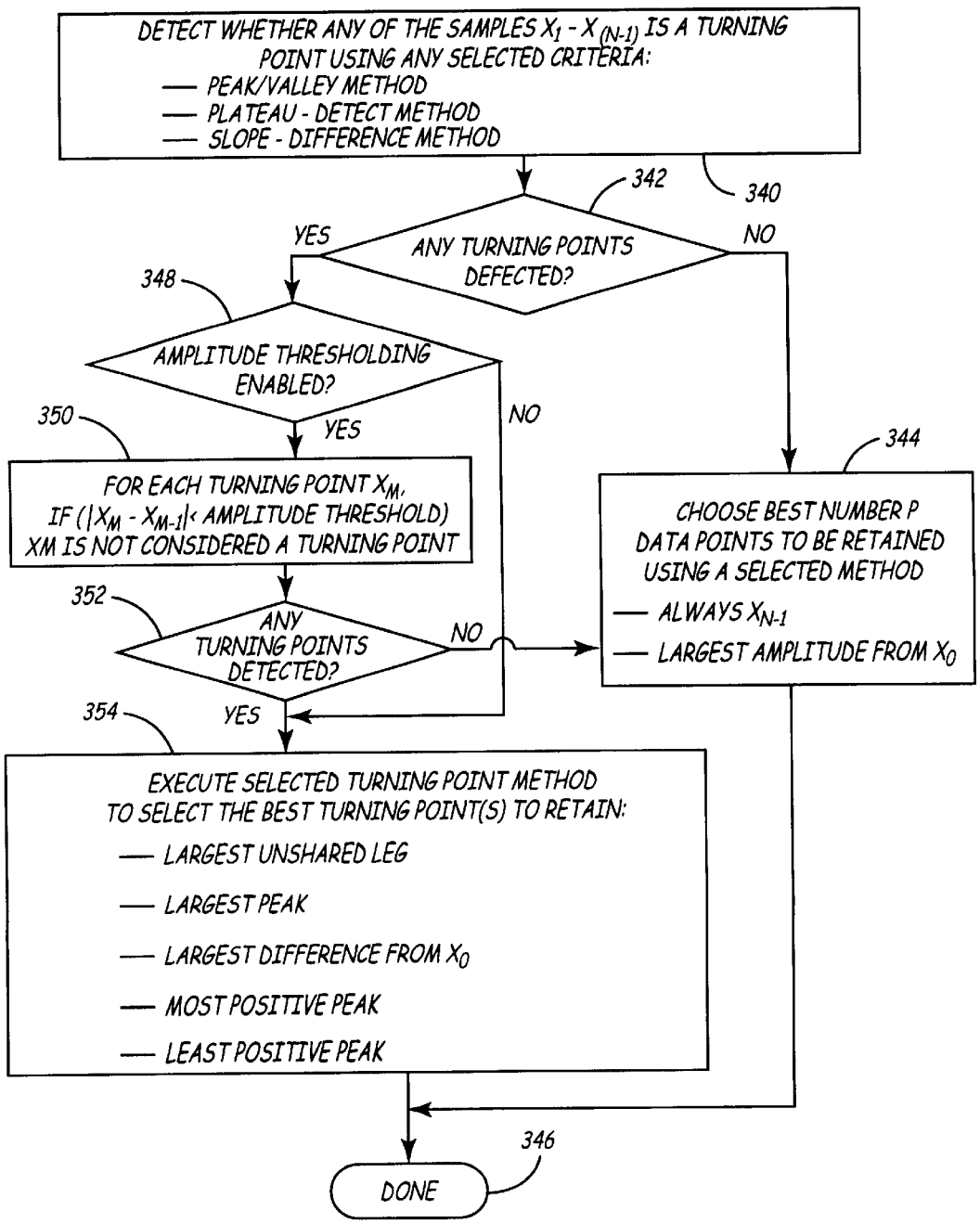
FIG. 15 is a flowchart illustrating the best turning point mechanisms of the current system, and includes the sub-steps associated with Step 318 of FIG. 14.

FIG. 15 is a flowchart illustrating the best turning point mechanisms of the current system, and includes the substeps associated with Step 318 of FIG. 14. In Step 340, data samples $X_0$–$X_N$ are used to determine which, if any, of the data points $X_1$ through $X_{(N-1)}$ are turning points. This may be accomplished in any of the ways discussed above. For example, any of the peak/valley, the plateau-detect, or the slope-difference methods may be used to detect turning points. Other variations of these detection methods may be contemplated by one skilled in the art.

After all of the turning points have been identified from among the data points XI through $X_{(N-1)}$, if no turning points were detected as determined by Step 342, execution proceeds to Step 344. The best P data points are selected for retention using some predetermined criterion in a manner discussed above. For example, assuming P is set to 1, data sample $X_{(N-1)}$ may be selected for retention. Alternatively, the data point that represents the largest amplitude change from the last retained point may be retained. When the number of P data points are selected for retention, execution is completed, as indicated by Step 346.

Returning to Step 342, if at least one turning point is detected, execution proceeds to decision Step 348, where it is determined if amplitude thresholding is enabled. If so, the difference in amplitudes between each turning point $X_M$ and a predetermined data point that is contiguous to data point $X_M$ in the sample stream is determined. If the amplitude difference is greater than a predetermined amplitude threshold, the data point $X_M$ is not considered a turning point. For example, Step 350 illustrates that if the absolute value of the difference between the amplitudes of data points $X_M$ and $X_{(M+1)}$ is less than a predetermined threshold value, $X_M$ is not considered a turning point. The contiguous data point $X_{(M+1)}$ could also be used in this calculation instead of data point $X_{(M-1)}$, if desired.

After turning points are eliminated based on the amplitude thresholding of Step 350, processing continues with Decision Step 352 wherein it is determined whether any turning points were detected. If not, processing continues with Step 344 in the manner discussed above. However, if turning points remain to be processed, processing continues with Step 354. In this step, one of the best turning point detection mechanisms is employed to select P data points for retention from among those turning points that were identified in the foregoing steps. The selected mechanism,used to make this selection may be programmable, and may be chosen to match the data set being processed. Alternatively, the same mechanism may always be selected. Some of the mechanisms discussed above for this purpose include the largest unshared leg method, the largest peak method, the largest difference from $X_0$ method, and the most positive and least positive peak methods.

One skilled in the art will readily appreciate that combinations of the exemplified best turning point mechanisms may also be devised. For example, if P is set to "two", a best turning point mechanism may be used that retains the data points associated with the largest unshared leg and the most positive peak (assuming these are not the same data points.) It may also be noted that if P is greater than the number of identified data points, some mechanism will be used to select one or more of the data samples that are not turning points for retention. Processing is then considered complete, as indicated by Step 346.

Figure 16:
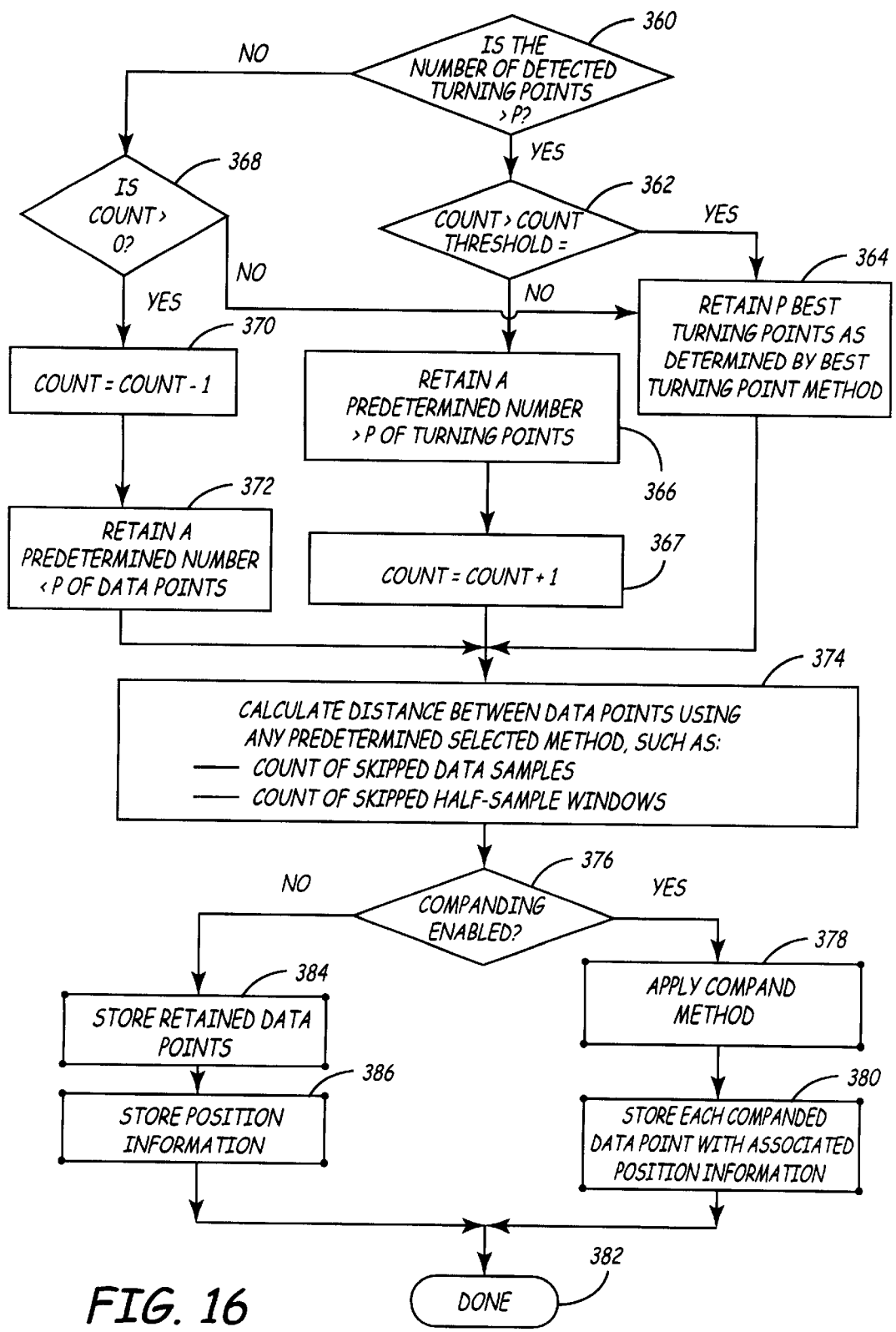
FIG. 16 is a flowchart illustrating the steps associated with execution of the variable compression method of Step 324 of FIG. 14.

FIG. 16 is a flowchart illustrating the steps associated with execution of the variable compression method of Step 324 of FIG. 14. According to this method, the number of data samples selected for retention will vary based on the frequency of the sampled signal, and on the number of "excess" data samples that have already been retained. In Step 360, it is determined whether more than the number of P turning points was detected in Step 318. If so, processing continues with decision Step 362, where it is determined whether the count of "excess" retained data samples as stored in variable "Count" is greater than a predetermined Count Threshold. This Count Threshold may be a programmable value, or may be set to a constant value. If the number stored in variable Count is greater than the predetermined Count Threshold, no extra data samples may be selected for retention. Therefore, processing continues with Step 364 where only the best P turning points are selected for retention. This selection can be made by applying one of the selected criterion shown in Step 354 (FIG. 15) to the identified turning points in a manner similar to that discussed above.

If the number stored in variable Count is not greater than the predetermined Count Threshold, more than P data samples may be selected for retention. In this instance, execution continues with Step 366, where a predetermined number that is greater than P data samples are selected from among the identified turning points. This selection can be made using a selected one of the mechanisms shown in Step 354. Since a predetermined number greater than P data samples are selected for retention, the count of the excess number of retained data points is incremented in Step 367.

Returning again to Step 360, if the number of detected turning points is less than, or equal to P, execution continues with decision Step 368. In this Step, it is determined whether variable Count is set to an integer greater than zero. If so, the count is decremented by one, and a predetermined number of data samples is retained, wherein that predetermined number is less than P. This is shown in Steps 370 and 372, respectively. Processing then continues to Step 374. If in Step 368 it is determined that the variable Count is not greater than zero, processing continues to Step 364, wherein P data samples are retained.

Continuing with Step 374, in this step the distance between retained data points is calculated. This may be performed using any of the methods discussed above. For example, a count may be generated to represent the number of data samples that were skipped between two contiguous retained data samples. Alternatively, a count of the number of skipped half-sample windows may be generated for each pair of contiguous retained data samples. Processing then proceeds to Step 376 wherein it is determined whether companding is enabled. If so, a companding method is applied in Step 378. This may including any of the mechanisms discussed above, including a divide-by-four mechanism, or a tiered mechanism wherein signals are scaled by a scale factor that is dependent on the original data sample amplitude. Finally, the companded data sample is stored with the associated position information as illustrated in Step 380. The position information may be stored in the same addressable storage located with the companded amplitude information, or in a different addressable storage location. Processing is then completed, as shown by Step 382.

If companding is not enabled in Step 376, processing continues with Step 384. In this step, the retained data points are stored. The position information is also stored, as indicated by Step 386. As stated above, the amplitude information may or may not be stored within the same addressable storage location as the associated position data, depending on implementation.

Figure 17:
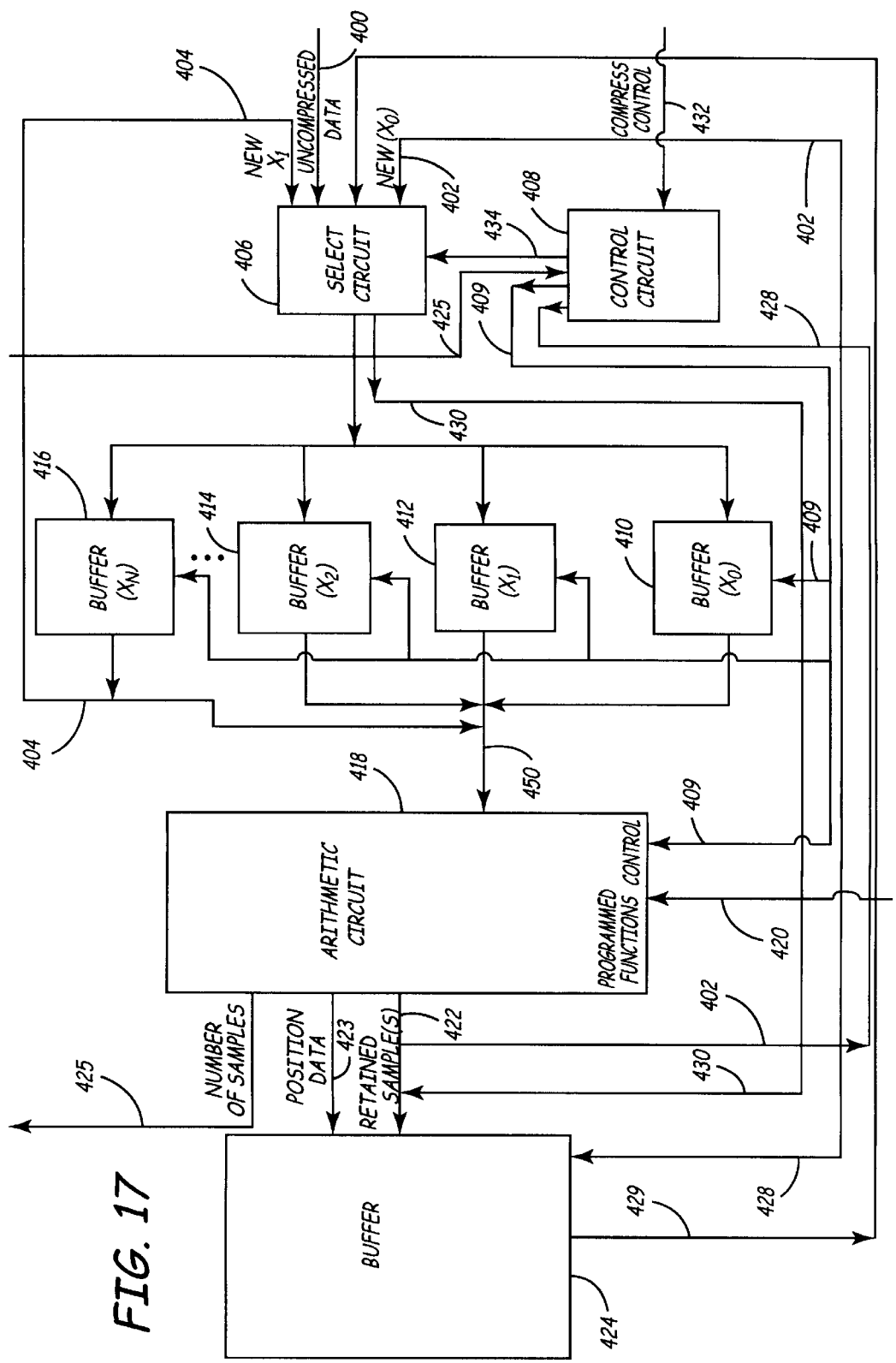
FIG. 17 is a block diagram of a processing circuit that may perform the compression function of the current invention.

FIG. 17 is a block diagram of a processing circuit that may perform the compression function of the current invention. This processing circuit may be that shown as processing circuit 151 located in controller/timer circuit 150. In this case, controller/timer circuit 150 may receive the sampled data directly from a sampling circuit (not shown) within controller/timer circuit 150, or from a temporary storage device such as that shown as storage device 153. Alternatively, processing circuit may be located in microcomputer circuit 132, such as the processing circuit 135. In this instance, processing circuit 135 may receive data directly from data communication bus 148 as it is provided to microcomputer circuit 132. Alternatively, data may be first stored in either RAM 142 or 137, and later retrieved during the compression process.

It yet another embodiment, IPG 10 does not include either processing circuit 151 or processing circuit 135, but instead performs compression via microprocessor 138, which operates under the control of firmware and/or software. The various embodiments of the invention are discussed further below.

Returning now to a discussion of FIG. 17, the illustrated circuitry receives uncompressed data points on line 400. The uncompressed data points are retained from a sampled signal, and have been converted to a digital format. Each sample includes a predetermined number of binary digits (bits), which may be eight or some other predetermined number.

During the first iteration of the compression function all data points $X_0$–$X_N$ will be received on line 400, assuming cascading is not being performed. During subsequent iterations, the value of $X_0$ is provided on line 402 and the value of $X_1$ is provided on line 404 in a manner to be discussed further below.

All samples are provided to select circuit 406. Select circuit, operating under the control of control circuit 408, provides sampled data $X_0$–$X_N$ to buffer circuits shown as buffer circuits 410, 412, 414, and 416 respectively. The number of buffer circuits used will depend on the number of data points included in the sample window. Enabling of these buffers is provided by control circuit 408 via control lines 409. The stored values $X_0$–$X_N$ are thereafter provided to arithmetic circuit 418, which may be any type of application-specific integrated circuitry, discrete components, or any combination thereof. Arithmetic circuit performs turning point detection and selection on the signal values according to a selected one of the best turning point criteria discussed above. Sequencing and control for arithmetic circuit is provided by control signals on line 409 provided by control circuit 408. The best turning point method may be programmably-selected based on the data set that is being compressed, or a particular criterion may be permanently selected.

In one embodiment, the turning point detection and selection methods may be programmably selected by signals on line 420, which are provided either by microprocessor 140 or some other source. Using this programmable capability, the best turning point criteria may be selected to match the data set. For example, the "most-positive" criteria may be selected if the data set is related to a waveform wherein the high-amplitude, positive signals are of more interest than the less positive signals.

Arithmetic circuit 418 will process data points $X_0$–$X_N$ based on the selected one of the best turning point methods, which may include any of those discussed above. In response, arithmetic circuit provides a predetermined number of retained samples on lines 422 to be stored in buffer circuit 424. Buffer circuit may be located in storage device 153, in RAM 142 or 137, or in some embedded storage within the processing circuit (not shown). The data points that are not retained may be discarded. In one embodiment of the invention, position data on lines 423 is also supplied to buffer circuit 424 to indicate the relative position of the data points. This is necessary when a variable number of samples are retained depending on input signal frequency.

Addressing of buffer circuit 424 is controlled by control circuit 408. In one embodiment of the invention, control circuit 408 receives a signal from arithmetic circuit 418 on line 425 indicating the number of samples to be stored for a given sample window. In response, control circuit 408 provides control lines 428 to initiate the appropriate number of storage sequences to buffer circuit 424. The control lines 428 may include address information and other read/write signals to initiate storage operations to buffer circuit 424. Alternatively, the address signals may be generated internally within buffer circuit 424, with control signals 428 providing the access control. In embodiments in which a constant number of data samples are stored for each data sample window, the signal provided on line 425 is not necessary.

In addition to being stored in buffer 424, the most recently-retained data point is also provided on line 402 to select circuit 406 to be used as the value $X_0$ during the next compression iteration. During this next iteration, data sample $X_N$ from the previous iteration is received on line 404 as $X_1$ for the current iteration. New values for $X_2$ and $X_N$ are received on line 400 if cascading is not enabled. Processing continues until the final uncompressed data point is received for compression on line 400. If fewer than all N samples are available during the last iteration, the remaining samples may be discarded, or alternatively, all samples may be written to buffer 424 directly on line 430 under the control of control circuit 408, which provides control lines to buffer 424 on line 428 in a manner discussed in the foregoing paragraphs.

As discussed above, cascading may be used to further compress previously-compressed sampled data. For example, applying the improved turning point compression method to data samples that have already undergone two-to-one compression will yield four-to-one data compression. If cascading is desired, control circuit 408 may initiate the retrieval of previously-compressed data signals from buffer 424 via the assertion of control signals on lines 428. The retrieved data is provided on lines 429 so that additional compression may be achieved. During the additional cascading steps, compressed data provided by the additional compression step may be stored within buffer 424 in a different memory range from the originally-compressed data. Alternatively, the compressed data may be stored in the same memory range as the originally-compressed data such that the originally-compressed data is overwritten. If increased compression speed is desired, an additional compression circuit similar to that shown in FIG. 8 may be provided to compress the previously-compressed data as it becomes available within buffer 424.

It will be appreciated by one skilled in the art that FIG. 17 is an illustration of one implementation of the current invention, and many other implementations are possible. For example, the functionally illustrated in FIG. 17 may be included in software or firmware. Buffers 410 through 416 may be registers included in microprocessor 134, or may be locations in RAM 142 or RAM 137. Loading of these buffers may be performed by microprocessor 134 under the control of software and/or firmware stored in RAM 142, ROM 144, or memory unit 136. Therefore, in this embodiment, select circuit 406 and/or control circuit 408 may not be needed. The uncompressed data stream may be received by microprocessor 134 directly from controller timer circuit 150 via data communication bus 148, or may be retrieved by microprocessor 134 from RAM 142 or RAM 137. Arithmetic circuit 218 could be implemented by an arithmetic unit included in microprocessor 134 operating under the control of the software and/or firmware. Furthermore, the processing circuit illustrated in FIG. 17 may be employed in any implantable device in which data compression is desired, or may further be included in any external device.

Figure 18:
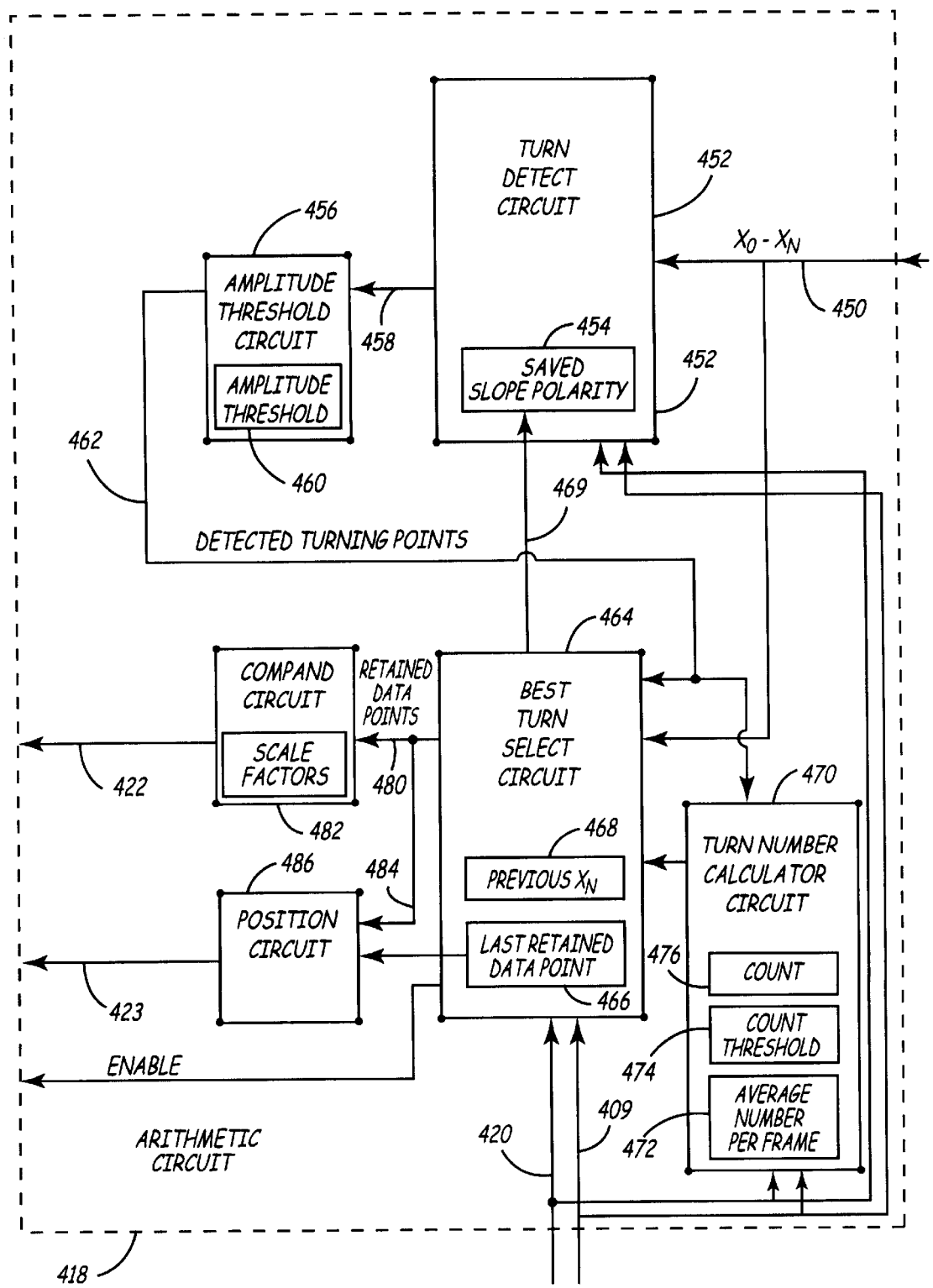
FIG. 18 is a block diagram of the arithmetic circuit 418 of FIG. 17.

FIG. 18 is a block diagram of the arithmetic circuit 418 of FIG. 17. Arithmetic circuit performs the turning point detection and selection functions under the control of sequencing signals provided on lines 409 by control circuit 408 of FIG. 17. The data samples are received on lines 450 from buffers 410 through 416 of FIG. 17. The data samples are provided to turn detect circuit 452, which implements one of the turn detection mechanisms discussed above. If desired, the implemented one of the turn detection mechanisms could be programmable based on the data set being processed. Programmable parameters could be provided on line 420, for example, by microprocessor 134, or by any of the other mechanisms discussed above. If the turn detect circuit 452 is employing the slope-difference method of turn detection, this circuit may include a storage device 454 to store the polarity of the slope of the line between the last two saved data samples.

In one embodiment of the invention, turn detect circuit 452 provides an indication of the detected turning points to amplitude threshold circuit 456 on line 458. Amplitude threshold circuit will determine, based on a predetermined threshold value shown stored in storage device 460, whether any of the turning points detected by turn detect circuit 452 should be eliminated from consideration as turning points. As discussed above, this may be desirable to eliminate low-amplitude turns that are most-likely the result of noise. In one embodiment, the amplitude threshold stored in storage device 460 is programmable.

Amplitude threshold circuit 456 provides an indication of any remaining turning points on line 462 to best turn select circuit 464. Best turn select circuit uses a selected mechanism which may be any of those discussed above to select a predetermined number of the best turning points. The best turning points are selected using a sample window of $X_0$ through $X_N$ data samples, wherein data samples $X_1$ through $X_{(N-1)}$ are considered for possible retention. Best turn select circuit 464 is shown to include several storage devices 466 and 468 for storing the last retained data point and the $X_N$ value from the previous compression iteration, respectively. These are used during a current data compression iteration as data samples $X_0$ and $X_1$, respectively, as discussed above. In one embodiment, a signal is also provided on line 469 to turndetect circuit 452 to indicate a non-zero slope polarity value. This value, which is saved in storage device 454, may be used by turn detect circuit to detect slopes using a slope-difference detection method.

In an embodiment employing a variable compression rate, the number of turns to be retained during a given compression iteration is determined by a turn number calculator circuit 470. This circuit uses a predetermined average number of samples to be stored per compression iteration, a count threshold value, and a running count of "excess" retained data sampled to make the determination of the number of data samples to be retained in a given sample window in the manner discussed above. These values are shown stored in storage devices 472, 474, and 476, respectively. The average number of samples to be stored per compression iteration and the count threshold value may be programmably set in one embodiment. The count value is initialized to zero at the start of the data compression process, and prior to each cascading iteration.

After best turn select circuit 464 determines which data point(s) will be retained during the current iteration, the retained samples may be provided on line 480 to compand circuit 482. Compand circuit 482 will compand the data by dividing the amplitude by a predetermined scale factor. The scale factor may vary depending on the amplitude of the signal so that, for example, high-amplitude signals are companded by a larger scale factor in the manner discussed above. The companded data signals are provided on line 422 to buffer circuit 424 of FIG. 17 for storage.

In an embodiment using a variable compression rate, best turn select circuit 464 provides an indication of which ones of the data samples are retained on line 484. This information is used by position circuit 486, along with an indication of which data sample was last retained, to generate position data. The position data indicates a relative distance between two consecutive retained data samples in the manner discussed above. Position data is provided on line to be saved with sample data in buffer circuit 424 (FIG. 17).

Reconstruction of the Sampled Waveform Using the Compressed Data

Data stored within a storage unit of an implantable medical device may be transferred to an external device via a telemetry uplink session, for example. This data may then be displayed. In the case of data samples that were not companded, and that were obtained using a constant compression ratio, the data samples may be used directly to re-construct the waveform without undergoing any pre-processing steps. The re-constructed waveform is, of course, only an approximation of the original signal, since some information is lost because of the finite sampling rate and the data compression function.

If the compressed data was companded using a selected transfer function, the data may be re-scaled using the appropriate inverse transfer function. This may be accomplished using logic that performs the inverse transfer function, or may be performed using a look-up table of the type known in the art. It may be noted that some resolution of the amplitude data is lost during the companding process, and the re-constructed waveform will therefore be an approximation of the originally-sampled waveform. However, the reconstruction will be accurate enough for most purposes.

In some cases, the compressed data may be associated with position data in the manner discussed above. This position data may be stored with associated amplitude data in a same addressable memory location as shown in FIG. 10, or may be stored in a different addressable memory location, as shown in FIG. 11. In this instance, the waveform re-construction process extracts this position information from the compressed data stream. The position data is then used to create the appropriate spacing between consecutive data samples so that the sampled waveform may be reconstructed. If the position data was calculated at a frequency that is less than the data sampling rate, some position information was lost during the compression process. Therefore, the reconstructed waveform will be an approximation of the original signal, but will provide the information needed for most diagnostic purposes.

While various embodiments have been illustrated herein, it will be understood that they are exemplary in nature only, and not limiting.

What is claimed is:

1. A method of performing data compression on a stream of data samples of a physiologic waveform, comprising the steps of:

obtaining data points as a data sample window;

determining whether consecutive data points of the obtained data points correspond to turning points; and determining, in response to the consecutive data points corresponding to turning points, which of the consecutive data points is to be retained, wherein the data sample window includes a first data point, a second data point, a third data point, and a fourth data point, the second data point and the third data point being the consecutive data points, and wherein, in response to both the second data point and the third data point corresponding to a turning point, the step of determining which of the consecutive data points is to be retained comprises the steps of:

calculating a first waveform amplitude corresponding to the first data point and the second data point and a second waveform amplitude corresponding to the third data point and the fourth data point;

retaining the second data point in response to the first waveform amplitude being greater than the second waveform amplitude; and retaining the third data point in response to the second waveform amplitude being greater than the first waveform amplitude.

2. The method of claim 1, wherein the step of determining which of the consecutive data points is to be retained further comprises the steps of:

retaining, in response to only one of the second data point and the third data point corresponding to a turning point, the only one of the second data point and the third data point as a turning point; and retaining the third data point as a turning point in response to neither of the second data point and the third data point corresponding to a turning point.

3. The method of claim 2, further comprising the steps of:

determining a first amplitude of the second data point;

determining a second amplitude of the third data point; and disregarding the second data point as a turning point in response to a difference between the first amplitude and the second amplitude being less than a predetermined amplitude.

4. The method of claim 1, wherein, in response to neither of the second data point and the third data point corresponding to a turning point, the step of determining which of the consecutive data points is to be retained further comprises the steps of:

determining a first amplitude deviation between the first data point and the second data point and a second amplitude deviation between the first data point and the third data point;

retaining the second data point as a turning point in response to the second amplitude deviation being less than the first amplitude deviation; and retaining the third data point as a turning point in response to the second amplitude deviation being greater than the first amplitude deviation.

5. A method of performing data compression on a stream of data samples of a physiologic waveform, comprising the steps of:

obtaining data points as a data sample window;

determining whether consecutive data points of the obtained data points correspond to turning points; and determining, in response to the consecutive data points corresponding to turning points, which of the consecutive data points is to be retained, wherein the data sample window includes a first data point, a second data point, a third data point, and a fourth data point, the second data point and the third data point being the consecutive data points, and wherein the step of determining whether consecutive data points of the obtained data points correspond to turning points comprises the steps of:

determining a first polarity of slopes of lines between the first data point and the second data point and between the second data point and the third data point, wherein the second data point is determined to be a turning point in response to the first polarity of slopes being a negative polarity; and determining a second polarity of slopes of lines between the second data point and the third data point and between the third data point and the fourth data point, wherein the third data point is determined to be a turning point in response to the second polarity of slopes being a negative polarity.

6. A method of performing data compression on a stream of data samples of a physiologic waveform, comprising the steps of:

obtaining data points as a data sample window;

determining whether consecutive data points of the obtained data points correspond to turning points; and determining, in response to the consecutive data points corresponding to turning points, which of the consecutive data points is to be retained, wherein the data sample window includes a first data point, a second data point, a third data point, and a fourth data point, the second data point and the third data point being the consecutive data points, and wherein, in response to both the second data point and the third data point corresponding to a turning point, the step of determining which of the consecutive data points is to be retained comprises the steps of:

calculating a first amplitude deviation corresponding to the second data point and a predetermined reference signal level and a second amplitude deviation corresponding to the third data point and the predetermined reference signal level;

retaining the second data point as a turning point in response to the second amplitude deviation being less than the first amplitude deviation; and retaining the third data point as a turning point in response to the second amplitude deviation being greater than the first amplitude deviation.

7. The method of claim 6, wherein the step of determining which of the consecutive data points is to be retained further comprises the steps of:

retaining, in response to only one of the second data point and the third data point corresponding to a turning point, the only one of the second data point and the third data point as a turning point; and retaining the third data point as a turning point in response to neither of the second data point and the third data point corresponding to a turning point.

8. A method of performing data compression on a stream of data samples of a physiologic waveform, comprising the steps of:

obtaining data points as a data sample window;

determining whether consecutive data points of the obtained data points correspond to turning points; and determining, in response to the consecutive data points corresponding to turning points, which of the consecutive data points is to be retained, wherein the data sample window includes a first data point, a second data point, a third data point, and a fourth data point, the second data point and the third data point being the consecutive data points, and wherein, in response to both the second data point and the third data point corresponding to a turning point, the step of determining which of the consecutive data points is to be retained comprises the steps of:

determining a first amplitude corresponding to the second data point and a second amplitude corresponding to the third data point;

retaining the second data point as a turning point in response to the second amplitude deviation being less than the first amplitude deviation; and retaining the third data point as a turning point in response to the second amplitude deviation being greater than the first amplitude deviation.

9. A method of performing data compression on a stream of data samples of a physiologic waveform, comprising the steps of:

obtaining data points as a data sample window;

determining whether consecutive data points of the obtained data points correspond to turning points; and determining, in response to the consecutive data points corresponding to turning points, which of the consecutive data points is to be retained, wherein the data sample window includes a first data point, a second data point, a third data point, and a fourth data point, the second data point and the third data point being the consecutive data points, and wherein, in response to both the second data point and the third data point corresponding to a turning point, the step of determining which of the consecutive data points is to be retained comprises the steps of:

determining a first amplitude corresponding to the second data point and a second amplitude corresponding to the third data point;

retaining the third data point as a turning point in response to the second amplitude being less than the first amplitude; and retaining the second data point as a turning point in response to the second amplitude being greater than the first amplitude.

10. A method of performing data compression on a stream of data samples of a physiologic waveform, comprising the steps of:

obtaining data points as a data sample window;

determining whether consecutive data points of the obtained data points correspond to turning points; and determining, in response to the consecutive data points corresponding to turning points, which of the consecutive data points is to be retained, wherein more than one criteria is utilized in the step of determining which of the consecutive data points is to be retained in response to more than one of the obtained data points correspond to turning points.

11. A method of performing data compression on a stream of data samples of a physiologic waveform, comprising the steps of:

obtaining data points as a data sample window;

determining whether consecutive data points of the obtained data points correspond to turning points;

determining, in response to the consecutive data points corresponding to turning points, which of the consecutive data points is to be retained; and applying a companding method to the data samples that are retained.

12. The method of claim 11, wherein the step of applying a companding method includes scale factors that vary depending on the amplitude of the data sample to which the companding method is being applied.

13. A method of performing data compression on a stream of data samples of a physiologic waveform, comprising the steps of:

obtaining data points as a data sample window;

determining whether consecutive data points of the obtained data points correspond to turning points; and determining, in response to the consecutive data points corresponding to turning points, which of the consecutive data points is to be retained, wherein the step of determining which of the consecutive data points is to be retained further comprises the step of calculating a predetermined number of data samples to retain.

14. The method of claim 13, wherein the predetermined number of data samples to retain is calculated to be greater than an average value of data samples retained within an average compression iteration if the number of data samples determined to be turning points is greater than the number of turning points detected during an average compression iteration.

15. The method of claim 14, further comprising the step of limiting the number of data samples retained if a predetermined number of previous compression iterations resulted in the predetermined number of data samples to retain being calculated as greater than the average value.

16. The method of claim 14, further comprising the step of calculating a distance value indicative of the distance between each respective pair of contiguous ones of retained data samples.

17. The method of claim 16, wherein each distance value expresses the distance between each respective pair of contiguous ones of retained data samples using an indication of sample frequency that is less than the frequency of the stream of data samples.

18. The method of claim 16, wherein the distance value for each respective pair of contiguous ones of retained data samples is stored in a same addressable storage location within a storage device as a predetermined one of the data samples included in the respective pair.

19. A system for compressing a stream of data samples of a physiologic waveform having corresponding data points, comprising:

a turn detect circuit receiving the data points as a data sample window and determining whether consecutive data points of the received data points correspond to turning points; and a best turn select circuit coupled to the turn detect circuit determining, in response to the consecutive data points corresponding to turning points, which of the consecutive data points corresponding to turning points is to be retained, wherein the data sample window includes a first data point, a second data point, a third data point, and a fourth data point, the second data point and the third data point being the consecutive datapoints, and wherein, in response to both the second data point and the third data point corresponding to a turning point, the best turn select circuit calculates a first waveform amplitude corresponding to the first data point and the second data point and a second waveform amplitude corresponding to the third data point and the fourth data point, retains the second data point in response to the first waveform amplitude being greater than the second waveform amplitude, and retains the third data point in response to the second waveform amplitude being greater than the first waveform amplitude.

20. The system of claim 19, wherein, in response to neither of the second data point and the third data point corresponding to a turning point, the turn detect circuit determines a first amplitude deviation between the first data point and the second data point and a second amplitude deviation between the first data point and the third data point, and retains the second data point as a turning point in response to the second amplitude deviation being less than the first amplitude deviation, and retains the third data point as a turning point in response to the second amplitude deviation being greater than the first amplitude deviation.

21. The system of claim 19, wherein the best turn circuit retains, in response to only one of the second data point and the third data point corresponding to a turning point, the only one of the second data point and the third data point as a turning point, and retains the third data point as a turning point in response to neither of the second data point and the third data point corresponding to a turning point.

22. The system of claim 21, wherein the turn detect circuit determines determining a first amplitude of the second data point, a second amplitude of the third data point, and disregards the second data point as a turning point in response to a difference between the first amplitude and the second amplitude being less than a predetermined amplitude.

23. A system for compressing a stream of data samples of a physiologic waveform, comprising:
   a turn detect circuit receiving data points as a data sample window and determining whether consecutive data points of the received data points correspond to turning points; and
   a best turn select circuit coupled to the turn detect circuit determining, in response to the consecutive data points corresponding to turning points, which of the consecutive data points corresponding to turning points is to be retained, wherein the data sample window includes a first data point, a second data point, a third data point, and a fourth data point, the second data point and the third data point being the consecutive data points, and wherein the best turn select circuit determines a first polarity of slopes of lines between the first data point and the second data point and between the second data point and the third data point, wherein the second data point is determined to be a turning point in response to the first polarity of slopes being a negative polarity, and wherein the best turn select circuit determines a second polarity of slopes of lines between the second data point and the third data point and between the third data point and the fourth data point, wherein the third data point is determined to be a turning point in response to the second polarity of slopes being a negative polarity.

24. A system for compressing a stream of data samples of a physiologic waveform, comprising:
   a turn detect circuit receiving data points as a data sample window and determining whether consecutive data points of the received data points correspond to turning points; and
   a best turn select circuit coupled to the turn detect circuit determining, in response to the consecutive data points corresponding to turning points, which of the consecutive data points corresponding to turning points is to be retained, wherein the data sample window includes a first data point, a second data point, a third data point, and a fourth data point, the second data point and the third data point being the consecutive data points, and wherein, in response to both the second data point and the third data point corresponding to a turning point, the turn detect circuit calculates a first amplitude deviation corresponding to the second data point and a predetermined reference signal level and a second amplitude deviation corresponding to the third data point and the predetermined reference signal level, and retains the second data point as a turning point in response to the second amplitude deviation being less than the first amplitude deviation and the third data point as a turning point in response to the second amplitude deviation being greater than the first amplitude deviation.

25. The system of claim 24, wherein the turn detect circuit retains, in response to only one of the second data point and the third data point corresponding to a turning point, the only one of the second data point and the third data point as a turning point, and retains the third data point as a turning point in response to neither of the second data point and the third data point corresponding to a turning point.

26. A system for compressing a stream of data samples of a physiologic waveform, comprising:
   a turn detect circuit receiving data points as a data sample window and determining whether consecutive data points of the received data points correspond to turning points; and
   a best turn select circuit coupled to the turn detect circuit determining, in response to the consecutive data points corresponding to turning points, which of the consecutive data points corresponding to turning points is to be retained, wherein the data sample window includes a first data point, a second data point, a third data point, and a fourth data point, the second data point and the third data point being the consecutive data points, and wherein, in response to both the second data point and the third data point corresponding to a turning point, the turn detect circuit determines a first amplitude corresponding to the second data point and a second amplitude corresponding to the third data point, and retains the second data point as a turning point in response to the second amplitude deviation being less than the first amplitude deviation, and the third data point as a turning point in response to the second amplitude deviation being greater than the first amplitude deviation.

27. A system for compressing a stream of data samples of a physiologic waveform, comprising:
   a turn detect circuit receiving data points as a data sample window and determining whether consecutive data points of the received data points correspond to turning points; and
   a best turn select circuit coupled to the turn detect circuit determining, in response to the consecutive data points corresponding to turning points, which of the consecutive data points corresponding to turning points is to be retained, wherein the data sample window includes a first data point, a second data point, a third data point, and a fourth data point, the second data point and the third data point being the consecutive data points, and wherein, in response to both the second data point and the third data point corresponding to a turning point, the turn detect circuit determines a first amplitude corresponding to the second data point and a second amplitude corresponding to the third data point, and retains the third data point as a turning point in response to the second amplitude being less than the first amplitude, the second data point as a turning point in response to the second amplitude being greater than the first amplitude.

28. A system for compressing a stream of data samples of a physiologic waveform, comprising:

a turn detect circuit receiving data points as a data sample window and determining whether consecutive data points of the received data points correspond to turning points; and a best turn select circuit coupled to the turn detect circuit determining, in response to the consecutive data points corresponding to turning points, which of the consecutive data points corresponding to turning points is to be retained, wherein more than one criteria is utilized to determine which of the consecutive data points is to be retained in response to more than one of the obtained data points correspond to turning points.

29. A system for compressing a stream of data samples of a physiologic waveform, comprising:

a turn detect circuit receiving data points as a data sample window and determining whether consecutive data points of the received data points correspond to turning points;

a best turn select circuit coupled to the turn detect circuit determining, in response to the consecutive data points corresponding to turning points, which of the consecutive data points corresponding to turning points is to be retained; and a compand circuit companding the data samples that are retained.

30. The system of claim 29, wherein compand circuit includes scale factors that vary depending on the amplitude of the data sample.

31. A system for compressing a stream of data samples of a physiologic waveform, comprising:

a turn detect circuit receiving data points as a data sample window and determining whether consecutive data points of the received data points correspond to turning points; and a best turn select circuit coupled to the turn detect circuit determining, in response to the consecutive data points corresponding to turning points, which of the consecutive data points corresponding to turning points is to be retained, wherein the best turn select circuit calculates a predetermined number of data samples to retain.

32. The system of claim 31, wherein the predetermined number of data samples to retain is calculated to be greater than an average value of data samples retained within an average compression iteration if the number of data samples determined to be turning points is greater than the number of turning points detected during an average compression iteration.

33. The system of claim 32, wherein the number of data samples retained is limited in response a predetermined number of previous compression iterations resulting in the predetermined number of data samples to retain being calculated as greater than the average value.

34. The system of claim 32, wherein the best turn select circuit calculates a distance value indicative of the distance between each respective pair of contiguous ones of retained data samples.

35. The system of claim 34, wherein each distance value expresses the distance between each respective pair of contiguous ones of retained data samples using an indication of sample frequency that is less than the frequency of the stream of data samples.

36. The system of claim 34, wherein the distance value for each respective pair of contiguous ones of retained data samples is stored in a same addressable storage location within a storage device as a predetermined one of the data samples included in the respective pair.

* * * * *